United States Patent
Ohashi et al.

(10) Patent No.: US 7,531,801 B2
(45) Date of Patent: May 12, 2009

(54) SOLDER MATERIAL TEST METHOD AND APPARATUS, CONTROL PROGRAM AND COMPUTER-READABLE RECORDING MEDIUM

(75) Inventors: Katsumi Ohashi, Kyoto (JP);
Masanobu Horino, Kyoto (JP);
Yasuhiro Onishi, Kyoto (JP)

(73) Assignee: OMRON Corporation, Kyoto-Shi (JP)

( * ) Notice: Subject to any disclaimer, the term of this patent is extended or adjusted under 35 U.S.C. 154(b) by 254 days.

(21) Appl. No.: 11/356,437

(22) Filed: Feb. 17, 2006

(65) Prior Publication Data
US 2008/0156990 A1 Jul. 3, 2008

(30) Foreign Application Priority Data
Feb. 22, 2005 (JP) ............... 2005-046284

(51) Int. Cl.
*G01J 5/02* (2006.01)
(52) U.S. Cl. .................................. 250/341.1
(58) Field of Classification Search ............... 250/341.1
See application file for complete search history.

(56) References Cited

U.S. PATENT DOCUMENTS

| | | | | |
|---|---|---|---|---|
| 3,471,698 | A * | 10/1969 | Mausteller et al. | 250/351 |
| 4,481,418 | A * | 11/1984 | Vanzetti et al. | 250/338.1 |
| 4,792,683 | A * | 12/1988 | Chang et al. | 250/341.6 |
| 4,999,499 | A * | 3/1991 | Bhatt | 250/342 |
| 5,476,207 | A | 12/1995 | Peterson et al. | |
| 6,269,179 | B1 | 7/2001 | Vachtsevanos et al. | |
| 2003/0230718 | A1 | 12/2003 | Shelley et al. | |

FOREIGN PATENT DOCUMENTS

| | | |
|---|---|---|
| JP | 03-028760 | 2/1991 |
| JP | 05-99831 | 4/1993 |
| JP | 10-082737 | 3/1998 |

* cited by examiner

*Primary Examiner*—David P Porta
*Assistant Examiner*—Mark R Gaworecki
(74) *Attorney, Agent, or Firm*—Foley & Lardner LLP

(57) ABSTRACT

Provided is a solder material test method that reduces labor and time and is preferred in operation hygiene. Detected are a first intensity at a particular wave number of infrared radiation reflected from a test-sample solder material by illuminating light to the test-sample solder material and a second intensity at the particular wave number of infrared radiation reflected from a comparative-sample solder material by illuminating light to the comparative-sample solder material. Depending upon the first and second intensities detected, intensity differences and ratios are determined. Those may be absorbance differences or intensities of between an infrared radiation absorbance to test-sample solder material and an infrared radiation absorbance to comparative-sample solder material. From the intensity difference, intensity ratio, absorbance difference and absorbance ratio, the test-sample solder material is tested for deterioration degree relatively to the comparative sample.

23 Claims, 11 Drawing Sheets

| CHEMICAL NAME | CHEMICAL FORMULA | CONTENT (wt%) |
|---|---|---|
| TIN | Sn | 80 TO 90 |
| SILVER | Ag | 1 TO 3 |
| COPPER | Cu | LESS THAN 1 |
| DIETHYLENE GLYCOL MONOHEXYL ETHER | $C_6H_{13}(OCH_2CH_2)_2\text{-}OH$ | 2 TO 4 |
| 2-ETHYL-1, 3-HEXANEDIOL | $C_3H_7CH(OH)CH(C_2H_5)CH_2OH$ | LESS THAN 1 |
| ROSIN | $C_{19}H_{29}COOH$ | 4 TO 6 |

| NUMBER OF PRINTS | | 200 | 400 | 600 | 800 | 1000 | 1200 |
|---|---|---|---|---|---|---|---|
| VISCOSITY [Pa·s] | | 178.5 | 212 | 282.3 | 353.5 | 450.8 | 640 |
| ABSORBANCE DIFFERENCE | 1600 [cm-1] | 0.00901 | 0.01309 | 0.01587 | 0.01982 | 0.02145 | 0.02308 |
| | 1700 [cm-1] | -0.00858 | -0.01016 | -0.01434 | -0.01514 | -0.01997 | -0.02656 |

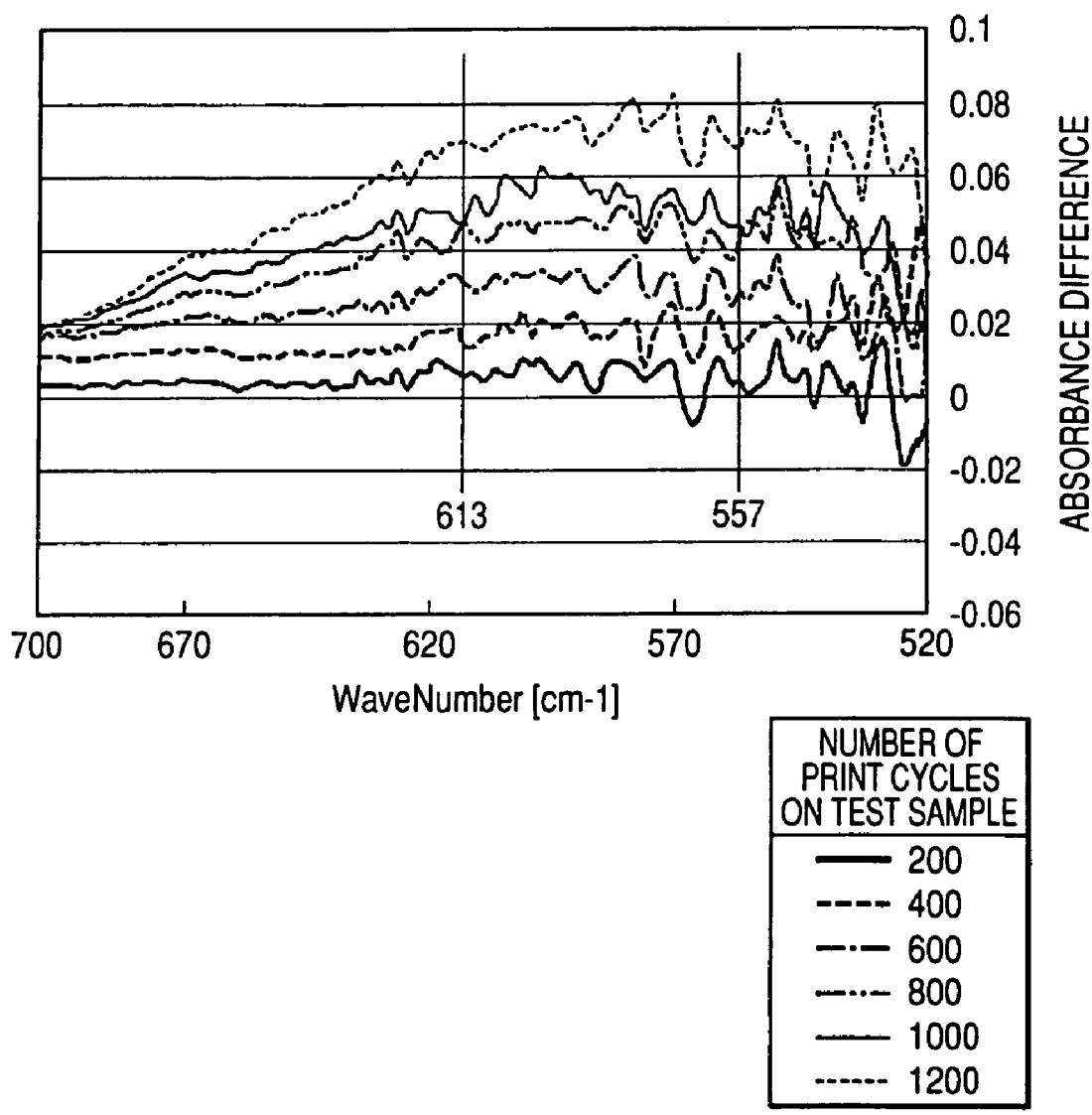

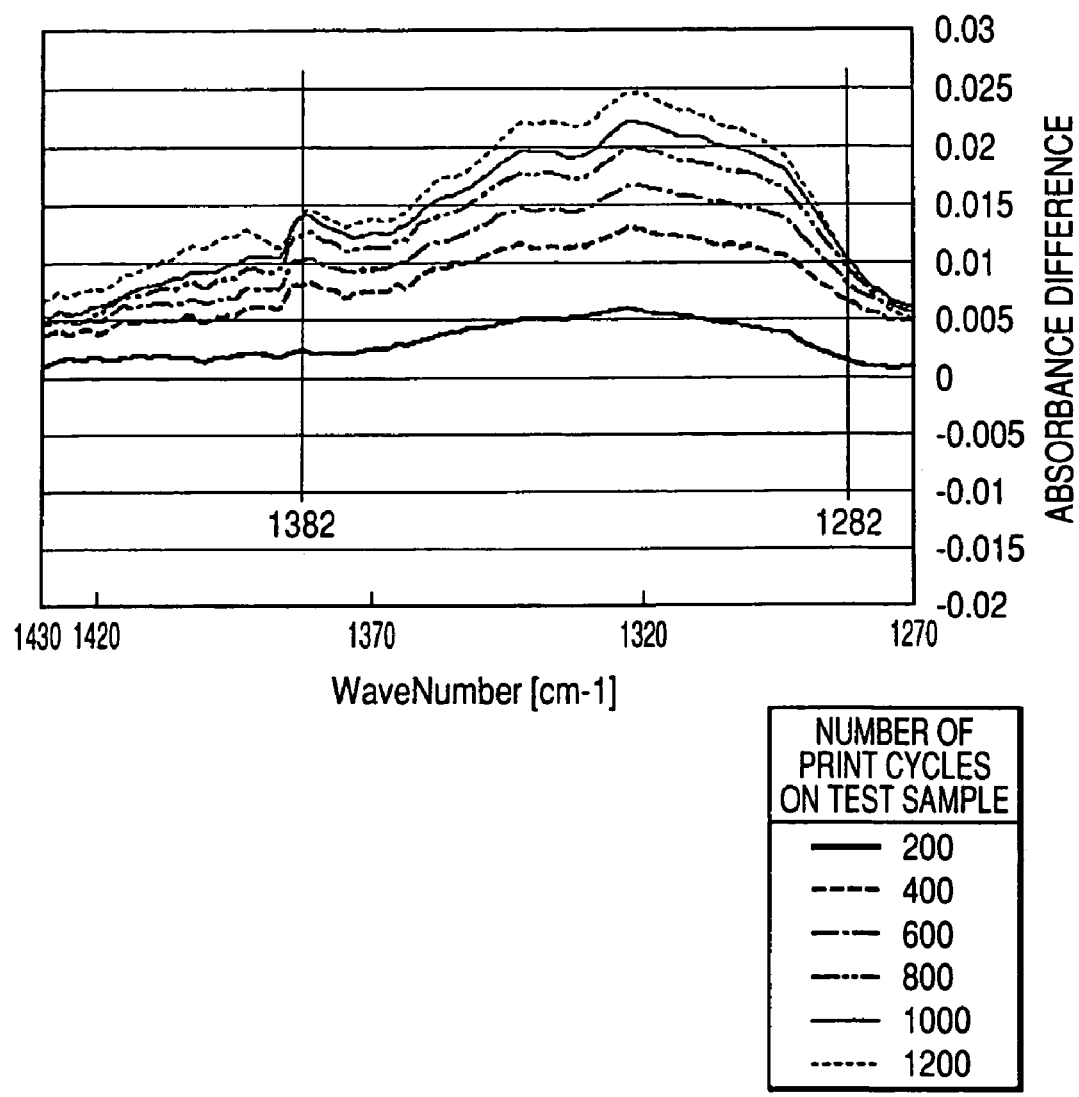

SOLDER MATERIAL TEST METHOD AND APPARATUS, CONTROL PROGRAM AND COMPUTER-READABLE RECORDING MEDIUM

BACKGROUND OF THE INVENTION

1. Field of the Invention

The present invention relates to a method and apparatus for testing a solder material for deterioration degree.

2. Description of the Related Art

On the production line of printed boards, electronic components are mounted onto the board by performing a printing process to print a solder material to a board, a mounting process to mount an electronic component onto the printed solder material and a reflow process to fix the electronic component on the board by soldering.

In the printing process, the solder material is put on the surface of a metal mask placed on the board. The metal mask is formed with an opening corresponding to a wiring pattern. The solder material on the metal mask surface is pushed and rotationally moved by a movable squeegee. Furthermore, the solder material being rotationally moved is squeezed out of the opening onto the board by the urging force of the movable squeegee. Based on this process, the solder material is printed to the board (see paragraph [0011] in JP-A-5-99831).

The metal mask is in continuous use for a number of boards, in a state where the same solder material is rested thereon. Accordingly, the solder material is rotationally moved by the movable squeegee repeatedly each time printing is performed. The solder material gradually deteriorates due to rotational movement, and the deteriorated solder material constitutes a factor causing defects on the printed board.

For this reason, when the solder material on the metal mask is analyzed in-line for deterioration degree and the solder material is deteriorated significantly, it is quite important to replace the solder material lying on the metal mask. In addition, before supplying a solder material onto the metal mask, it is important to analyze the deterioration degree of the solder material to supply and check whether or not there is a deterioration in the solder material before it is supplied.

Here, the solder material has a viscosity, oxidation degree and reducing power that serves as an index in evaluating the deterioration degree thereof. The reason the viscosity, oxidation degree and reducing power is used as an index is because of the following.

It is known that, as solder material deteriorates, its viscosity increases to proceed oxidation and lower the reducing power. Herein, it is also known that, when a highly viscous solder material is printed on the board, defects such as "breakages" or "blurs" readily occur on the board thus printed. Meanwhile, it is also known that, in case an oxidized solder material is printed to the board, inferiorities such as "solder balls" or "solder unfused" readily occur on the post-reflow board. Furthermore, it is also known that, when solder material which is lowered in reducing power is printed to a board, such an inferiority as "wettability reduction" readily occurs on the post-reflow board.

Namely, the viscosity, oxidation degree and reducing power of a solder material is correlated to the occurrence rate of printed board inferiorities. For this reason, the viscosity, oxidation degree and reducing power of a solder material serves as a significant index in evaluating the deterioration degree of a solder material.

Conventionally, there are various methods to analyze the deterioration degree of solder material, as exemplified in JP-A-5-99831 (date opened: Apr. 23, 1993), JP-B-8-20434 (date published: Mar. 4, 1996) and JP-A-10-82737 (date opened: Mar. 31, 1998).

JP-A-5-99831 discloses a method to measure the viscosity of a solder material depending upon a velocity of a solder material flowing on a squeegee surface. However, this method can measure the viscosity of a solder material only when driving the squeegee. Thus, there is a problem that the test sample is limited to a solder material being used in a printing process.

Consequently, JP-B-8-20434 discloses a method to measure the acid degree of a solder material (flux) by conducting a titration by use of a solder material sampled. However, in this method, there encounters a problem that labor and time is required in conditioning a reagent.

Meanwhile, JP-A-10-82737 discloses a technique to measure the surface oxidation rate of a solder material according to ultraviolet-ray photoelectron spectroscopy. However, this method uses ultraviolet radiation that is harmful to the human body, and hence is not preferred in view of operation hygiene.

SUMMARY OF THE INVENTION

It is an object of the present invention to provide a solder material test method and apparatus where labor and time are reduced in operation, and hence is preferred in operation hygiene.

In order to achieve the object, a solder material test method in the present invention includes: a first detecting step of detecting a first intensity at a particular wave number of infrared radiation reflected from a test-sample solder material by illuminating light to the test-sample solder material; a second detecting step of detecting a second intensity at the particular wave number of infrared radiation reflected from a comparative-sample solder material by illuminating light to the comparative-sample solder material; and a test step of testing a deterioration degree of the test-sample solder material relatively to the comparative-sample solder material, depending upon the first and second intensities detected.

It is known that a solder material of good quality is low in viscosity and oxidation degree, but high in reducing power wherein, when the solder material deteriorates, a viscosity/oxidation degree increases and reducing power decreases. Accordingly, the deterioration degree of a solder material can be determined from one of a viscosity, an oxidation degree and a reducing power of the solder material.

The present inventors have considered a technique that is different from the existing technique but can analyze at least one of viscosity, oxidation degree and reducing power of a solder material. As a result of eager devising, the present inventors have found that a solder material can be analyzed for at least one of viscosity, oxidation degree and reducing power by use of infrared spectroscopy.

Below is detailed the reason why a solder material can be analyzed for viscosity, oxidation degree or reducing power by an infrared spectroscopy.

Where a solder material is in continuous use or exposed to the external air, the metal contained in the solder material oxidizes and the acid contained (e.g. carboxylic acid) turns into a salt. Namely, when a solder material is used and is continuously exposed to the exterior air, the contained metal oxide increases, the contained acid decreases and the contained salt increases in the solder material.

The metal oxide increase raises the solder-material oxidation degree, the salt increase enhances the solder-material viscosity and acid content decrease lowers the solder-material reducing power.

For this reason, in case a test-sample solder material is to be analyzed for the content of metal oxide, acid and salt, the relevant solder material can be tested for viscosity, oxidation degree and reducing power, and eventually for solder-material deterioration degree. Namely, the content of metal oxide, acid and salt in a solder material is indicative of a deterioration degree (viscosity, oxidation degree and reducing power) of the solder material.

Here, the present inventors have realized that at least one of metal oxide, acid and salt contents can be analyzed by infrared spectroscopy, thus reaching a realization of the invention.

Specifically, the invention detects a first intensity at a particular wave number of infrared radiation reflected from the test-sample solder material due to illumination of light to the test-sample solder material, and a second intensity at the particular wave number of infrared radiation reflected from the comparative-sample solder material due to illumination of light to the comparative-sample solder material.

Here, in accordance with the content of metal oxide, acid and salt in a solder material, the solder material changes in absorption of infrared radiation at a particular wave number, thus changing the intensity at the particular wave number of infrared radiation reflected by the solder material. This is because the metal oxide, acid and salt contained in the solder material each have a property to absorb infrared radiation at a wave number band specified.

Accordingly, depending upon a first intensity at a particular wave number of infrared radiation reflected by a test-sample solder material and a second intensity at the particular wave number of infrared radiation reflected by a comparative-sample solder material, the test-sample solder material can be analyzed for metal oxide, acid and salt contents relative to those of the comparative-sample solder material. This makes it possible to test relatively the test-sample solder material for viscosity, oxidation degree and reducing power. Accordingly, the deterioration degree (viscosity, oxidation degree and reducing power) of the test-sample solder material can be tested relatively to the comparative-sample solder material.

In the solder material test method of the invention, the illumination light to the solder material may be infrared radiation at the particular wave number or light including infrared radiation at the particular wave number.

The solder material test method of the invention shown in the above does not require a titration as disclosed in JP-B-8-20434, thus further reducing the operational labor and time than the method in JP-B-8-20434. The solder material test method of the invention shown in the above does not use ultraviolet radiation, and hence is preferred rather than the method of JP-A-10-82737, in respect of operational hygiene.

Meanwhile, in order to achieve the foregoing object, a solder material test apparatus in the invention comprises: a light source that illuminates light to a test-sample solder material and a comparative-sample solder material; intensity detecting means that detects a first intensity at a particular wave number of infrared radiation reflected from the test-sample solder material due to illumination of the light, and a second intensity at the particular wave number of infrared radiation reflected from the comparative-sample solder material due to illumination of the light; and control means that outputs a deterioration parameter indicative of a comparative deterioration degree of the test-sample solder material relative to the comparative-sample solder material.

According to the above structure, the intensity detecting means detects a first intensity at a particular wave number of infrared radiation reflected from the test-sample solder material due to illumination of the light, and a second intensity at the particular wave number of infrared radiation reflected from the comparative-sample solder material due to illumination of the light.

Here, the intensity at a particular wave number of infrared radiation reflected the solder material changes in accordance with the metal oxide, acid and salt contents in the solder material. This is because the metal oxide, acid and salt contained in the solder material has a property to absorb infrared radiation at a wave number specified.

Accordingly, if depending upon a first intensity at a particular wave number of infrared radiation reflected from the test-sample solder material and a second intensity at the particular wave number of infrared radiation reflected from the comparative-sample solder material, it is possible to determine a content of metal oxide, acid and salt in the test-sample solder material relative to the comparative-sample solder material. Here, the content is indicative of a deterioration degree (viscosity, oxidation degree and reducing power) of the solder material.

Therefore, in the above structure, the relative content is outputted as a deterioration parameter indicative of a comparative deterioration degree of the test-sample solder material relative to the comparative-sample solder material. This allows the user of the apparatus to analyze the comparative content in the test-sample solder material relative to the comparative-sample solder material by means of deterioration parameters outputted, and hence to test the comparative deterioration degree in the test-sample solder material relative to the comparative-sample solder material.

Meanwhile, the solder material test method of the invention satisfactorily analyzes at least one of metal oxide, acid and salt contents. Accordingly, the particular wave number may be a wave number included in a wave number band of infrared radiation to be absorbed by the metal oxide included in the solder material. The metal oxide may be, for example, tin oxide or lead oxide.

Incidentally, the tin oxide and lead oxide has a property to absorb an infrared ray at $520$ $cm^{-1}$-$700$ $cm^{-1}$. Accordingly, the particular wave number is preferably a wave number included in a wave number band in a range of $520$ $cm^{-1}$-$700$ $cm^{-1}$.

Meanwhile, the solder material test method of the invention satisfactorily analyzes at least one of metal oxide, acid and salt contents. Accordingly, the particular wave number may be a wave number included in an infrared radiation wave number band to be absorbed by the acid included in the solder material. The acid is preferably carboxylic acid. This is because, of the acids included in the solder material, carboxylic acid can be taken as an acid much in content.

Incidentally, carboxylic acid has a property to absorb infrared radiation at $1665$ $cm^{-1}$-$1730$ $cm^{-1}$. Therefore, the particular wave number is preferably included in a range of $1665$ $cm^{-1}$-$1730$ $cm^{-1}$.

Furthermore, because the solder material test method is to satisfactorily analyze at least one of metal oxide, acid and salt, the particular wave number may be included in a wave number band where infrared radiation is absorbed by the salt contained in the solder material. The salt is preferably carboxylate. This is because, of the salts contained in the solder material, the salt much in content may be carboxylate.

Incidentally, carboxylate has a property to absorb infrared radiation at $1270$ $cm^{-1}$-$1430$ $cm^{-1}$. Therefore, the particular wave number is preferably in a range of $1270$ $cm^{-1}$-$1430$ $cm^{-1}$. Meanwhile, carboxylate has a property to absorb infrared radiation at $1500$ $cm^{-1}$-$1650$ $cm^{-1}$. Therefore, the particular wave number is preferably in a range of $1500$ $cm^{-1}$-$1650$ $cm^{-1}$.

The test step may be a procedure to determine a difference between the first intensity and the second intensity. The deterioration parameter may be a difference between the first intensity and the second intensity. The reason for this is as follows.

The difference is a parameter indicative of a difference degree in the infrared absorbance at the particular wave number between the test-sample solder material and the comparative-sample solder material. Namely, with such a difference, analysis can be made as to the difference in the content of metal oxide, carboxylic acid and carboxylate between the comparative sample solder material and the test-sample solder material, making it possible to comparatively conduct a test as to the viscosity, oxidation degree and reducing power of the test-sample solder material relative to the comparative-sample solder material, and hence as to the deterioration degree (viscosity, oxidation degree and reducing power) of the test-sample solder material.

The test step may be a procedure to determine a ratio of the first intensity and the second intensity. Furthermore, the deterioration parameter may be a ratio of the first intensity and the second intensity. The reason for this is as follows.

The difference is a parameter indicative of a difference degree in the infrared absorbance at the particular wave number between the test-sample solder material and the comparative-sample solder material. Namely, with such a difference, analysis can be made as to the difference in the content of metal oxide, carboxylic acid and carboxylate between the comparative sample solder material and the test-sample solder material, making it possible to comparatively conduct a test as to the viscosity, oxidation degree and reducing power of the test-sample solder material relative to the comparative-sample solder material, and hence as to the deterioration degree (viscosity, oxidation degree and reducing power) of the test-sample solder material.

Incidentally, there may be a difference between the intensity of infrared radiation included in the light illuminated to the comparative sample and the intensity of infrared radiation included in the light illuminated to the test sample. In this case, this difference is included in the difference between the first and second intensities detected.

Preferably, a reference wave number is established that is a wave number different from the particular wave number, to detect further a third intensity of infrared radiation at the reference wave number reflected from the test-sample solder material, and a fourth intensity of infrared radiation at the reference wave number reflected from the comparative-sample solder material, thereby correcting at least any of the first and second intensities depending upon a difference between the third and fourth intensities.

The test step may be a procedure to determine a first infrared radiation absorbance at the particular wave number to the test-sample solder material depending upon the first intensity, a second infrared radiation absorbance at the particular wave number to the comparative-sample solder material depending upon the first intensity, thereby determining a difference between the first infrared radiation absorbance and the second infrared radiation absorbance. Furthermore, the control means may determine a first infrared radiation absorbance at the particular wave number to the test-sample solder material depending upon the first intensity, a second infrared radiation absorbance at the particular wave number to the comparative-sample solder material depending upon the first intensity, thereby outputting, as a deterioration parameter, a difference between the first infrared radiation absorbance and the second infrared radiation absorbance. The reason for this is as follows.

The difference between the first and second infrared radiation absorbances is a parameter indicative of a difference degree in the infrared radiation absorbance at the particular wave number between the test-material solder material and the comparative-sample test material. Accordingly, with such a difference, analysis can be made as to the difference in the content of metal oxide, carboxylic acid and carboxylate between the comparative sample solder material and the test-sample solder material, making it possible to comparatively conduct a test as to the viscosity, oxidation degree and reducing power of the test-sample solder material relative to the comparative-sample solder material, and hence as to the deterioration degree (viscosity, oxidation degree and reducing power) of the test-sample solder material.

The test step may be a procedure to determine a first infrared radiation absorbance at the particular wave number to the test-sample solder material depending upon the first intensity, a second infrared radiation absorbance at the particular wave number to the comparative-sample solder material depending upon the first intensity, thereby determining a ratio of the first infrared radiation absorbance and the second infrared radiation absorbance. Furthermore, the control means may perform a processing to determine a first infrared radiation absorbance at the particular wave number to the test-sample solder material depending upon the first intensity, a second infrared radiation absorbance at the particular wave number to the comparative-sample solder material depending upon the first intensity, thereby outputting, as a deterioration parameter, a ratio of the first infrared radiation absorbance and the second infrared radiation absorbance. The reason for this is as follows.

The ratio of the first infrared radiation absorbance and the second infrared radiation absorbance is a parameter indicative of a difference degree in the infrared radiation absorbance at the particular wave number between the test-material solder material and the comparative-sample test material. Accordingly, with such a ratio, analysis can be made as to the difference in the content of metal oxide, carboxylic acid and carboxylate between the comparative sample solder material and the test-sample solder material, making it possible to comparatively conduct a test as to the viscosity, oxidation degree and reducing power of the test-sample solder material relative to the comparative-sample solder material, and hence as to the deterioration degree (viscosity, oxidation degree and reducing power) of the test-sample solder material.

There may be a difference between the intensity of infrared radiation included in the light illuminated to the comparative sample and the intensity of infrared radiation included in the light illuminated to the test sample. In this case, this difference is included in the difference between the first and second intensities detected, and hence in the difference between the first and second infrared radiation absorbances.

Accordingly, a reference wave number is satisfactorily established different in wave number from the particular wave number, to detect further a third intensity at the reference wave number of infrared radiation reflected from the test-sample solder material, and a fourth intensity at the reference wave number of infrared radiation reflected from the comparative-sample solder material. Furthermore, it is preferred to determine a third infrared radiation absorbance at the reference wave number to the test-sample solder material depending upon the third intensity, and a fourth infrared radiation absorbance at the reference wave number to the test-sample solder material depending upon the fourth intensity, thereby correcting at least any of the first and second infrared radiation absorbances depending upon a difference between the third infrared radiation absorbance and the fourth infrared radiation absorbance.

The control means may be realized by a computer. In this case, a control program for realizing the control means on the computer and a computer-readable recording medium recording the control program are within the scope of the invention.

As described so far, a solder material test method in the invention includes: a first detecting step of detecting a first intensity at a particular wave number of infrared radiation reflected from a test-sample solder material by illuminating light to the test-sample solder material; a second detecting step of detecting a second intensity at the particular wave number of infrared radiation reflected from a comparative-sample solder material by illuminating light to the comparative-sample solder material; and a test step of testing a deterioration degree of the test-sample solder material relative to the comparative-sample solder material, depending upon the first and second intensities detected.

Therefore, the metal oxide, acid and salt contents in a test-sample solder material can be analyzed relative to a comparative-sample solder material. This makes it possible to test the test-sample solder material for viscosity, oxidation degree and reducing power. Hence, the test-sample solder material can be tested for deterioration degree (viscosity, oxidation degree and reducing power) relative to the comparative-sample solder material.

BRIEF DESCRIPTION OF THE DRAWINGS

FIG. 4A is a chart showing, for each test sample, the absorbance differences, as to a plurality of test samples, obtained by subtracting infrared radiation absorbance of comparative-sample solder material from an infrared radiation absorbance of test-sample solder material while FIG. 4B is a table showing the number of print cycles, viscosity and infrared radiation absorbance at predetermined wave number of a plurality of test samples;

FIG. 5 is a chart showing, for each test sample, the absorbance differences, as to a plurality of test samples, obtained by subtracting infrared radiation absorbance to comparative-sample solder material from infrared radiation absorbance to test-sample solder material, in a wave-number band of 520 $cm^{-1}$-700 $cm^{-1}$;

FIG. 6 is a chart showing, for each test sample, the absorbance differences, as to a plurality of test samples, obtained by subtracting infrared radiation absorbance to comparative-sample solder material from infrared radiation absorbance to test-sample solder material, in a wave-number band of 1270 $cm^{-1}$-1420 $cm^{-1}$;

DESCRIPTION OF THE PREFERRED EMBODIMENTS

Solder Material Test Method

Figures 1, 2:
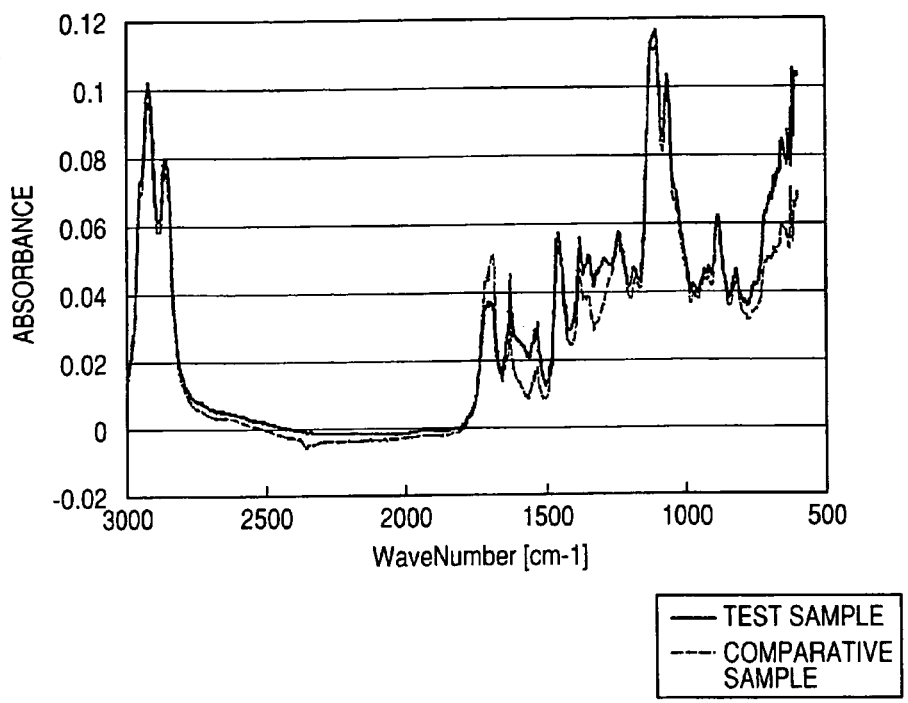
FIG. 1 is a spectrum chart, showing an infrared radiation absorbance of a test-sample solder material and an infrared radiation absorbance of a comparative-sample solder material, obtained by a solder material test method in an example of the invention.
FIG. 2 is a table showing ingredients and a composition (by weight %) of a test-sample solder material in the solder material test method in an example of the invention.

A solder material test method in this embodiment uses infrared radiation, to test a solder material for deterioration degree by using infrared radiation. Note that "solder material" in the embodiment signifies a creamy solder paste for use on a production line for a printed board. In the invention, however, it is not limited to such a solder paste but is applicable generally to the solder materials well known.

Now the solder material test method in the embodiment is detailed in the below.

When a solder material is continuously used or exposed to the external air, the metal in the solder oxidizes and the carboxylic acid therein turns into carboxylate. Namely, when a solder material is used or continuously exposed to the external air, the metal oxide contained increases, the carboxylic acid contained decreases and the carboxylate contained increases in the solder material.

There arises a phenomenon that the solder material is increased in oxidation degree by the increase of metal oxide, increased in viscosity by the increase of carboxylic acid and decreased in reduction power by the content decrease of carboxylic acid. The phenomenon is called deterioration of a solder.

Accordingly, in case a test-sample solder material can be analyzed for at least one of metal oxide content, carboxylic acid content and carboxylate content, the solder material can be tested for at least one of viscosity, oxidation degree and reduction power, and ultimately for deterioration degree.

Meanwhile, it is known that each of metal oxide, carboxylic acid and carboxylate is to absorb infrared radiation at a particular wave-number band specified for same.

Accordingly, a solder material test method in this embodiment is realized by implementing a combination of the following steps. At first, a first detecting step is performed to detect a first intensity at a particular wave number of infrared radiation reflected from a test-sample solder material by illuminating light to the test-sample solder material. Then, a second detecting step is performed to detect a second intensity at the particular wave number of infrared radiation reflected from a comparative-sample solder material by illuminating light to the comparative-sample solder material. Based on the intensities thus detected, a test step is performed to test a deterioration degree of the test-sample solder material relatively to a deterioration degree of the comparative-sample solder material. Incidentally, the first and second detecting steps may be reverse or simultaneous in the order.

According to the solder material test method in the present embodiment, the first and second detecting steps are to detect a first intensity at a particular wave number of infrared radiation reflected from the test-sample solder material and a second intensity at a particular wave number of infrared radiation reflected from the comparative-sample solder material.

Here, metal oxide, carboxylic acid and carboxylate are each to absorb infrared radiation at a particular wave number band specified thereon. Accordingly, in accordance with the content of metal oxide, carboxylic acid and carboxylate in a solder material, the solder material is changed in the absorbing amount of infrared radiation at a particular wave number. This changes the intensity at a particular wave number of infrared radiation reflected the solder material.

Accordingly, if based on the intensities detected in the first and second detecting steps, it is possible to determine at least one of metal oxide, acid and salt contents in the test-sample solder material relatively to the comparative-sample solder material. Therefore, the test-sample solder material can be tested for deterioration degree relatively to the comparative-sample solder material.

Incidentally, the test step may be in the form of (a) a procedure to determine a difference between the first intensity and the second intensity, (b) a procedure to determine a ratio of the first intensity and the second intensity, (c) a procedure to determine a first infrared radiation absorbance at the particular wave number to test-sample solder material from the first intensity and a second infrared radiation absorbance at the particular wave number to comparative-sample solder material from the second intensity, thereby determining a difference between the first and second infrared radiation absorbances, and (d) a procedure to determine a ratio of the first infrared radiation absorbance and the second infrared radiation absorbance.

The difference and the ratio are parameters each indicative of a difference degree in the infrared radiation absorbance at the particular wave number between the comparative-sample solder material and the test-sample solder material. By determining these parameters, it is possible to analyze the difference in the content of metal oxide, carboxylic acid and carboxylate between the comparative-sample solder material and comparative-sample solder material. This makes it possible to test the test-sample solder material for viscosity, oxidation degree and reducing power relatively to the comparative-sample solder material, and hence to test the test-sample solder material for deterioration degree (viscosity, oxidation degree and reducing power) relatively.

Incidentally, in the test step, in case the practicer for the solder material test method merely compares between the detected intensities without determining the difference or ratio, the test-sample solder material can be determined for deterioration degree relatively to the comparative-sample solder material.

Meanwhile, the test and comparative samples may use different solder materials or the same solder material.

Incidentally, the "use the same solder material" refers to such a case that, say, a solder material "a" in a new-product state is taken as a comparative sample while the solder material "a" in a post-use state (after a use in a board-print process) is taken as a test sample. Otherwise, a solder material "b", printed the number of print cycles 100 in a board-print process, may be taken as a comparative sample while the relevant solder material "b", printed the number of print cycles 200 be taken as a test sample.

EXAMPLE 1

Now described is an example of the solder material test method in this embodiment shown in the above.

A solder material to be tested is first described in this example. This example used, in the test, a solder material containing the ingredients shown in FIG. 2. As shown in the figure, the solder material in this example contains 80-90 percent of tin, 1-3 percent of silver, less than 1 percent of copper, 2-4 percent of diethylene glycol monohexyl ether, less than 1 percent of 2-ethyl-1,3-hexanediol and 4-6 percent of rosin.

Incidentally, although the solder material has the main ingredient of a metal, such as tin (Sn) or lead (Pb), the solder material in the example uses tin as such a metal, as shown in FIG. 2. Meanwhile, the solder material in this example employs rosin ($C_{19}H_{29}COOH$) as carboxylic acid, a main ingredient providing reducing power to the solder material, as shown in FIG. 2.

This example employed, as a comparative sample, a solder material having a composition shown in FIG. 2 and in a new-product state, and as a test sample a solder material used in a print process for a printed board. Incidentally, from now on, the comparative-sample solder material may be referred merely to as "comparative sample" while the test-sample solder material as "test sample".

Here, infrared radiation illumination was conducted at equal intensities respectively to the comparative and test samples, to detect the intensity (second intensity) of infrared radiation reflected the comparative sample at a band of 500 $cm^{-1}$-3000 $cm^{-1}$ and the intensity (first intensity) of infrared radiation reflected the test sample at a band of 500 $cm^{-1}$-3000 $cm^{-1}$ (first detection step, second detection step).

Furthermore, this example calculated, for each wave number, an absorbance of infrared radiation to the comparative sample (second infrared radiation absorbance) and an absorbance of infrared radiation to the test sample (first infrared radiation absorbance). Incidentally, the absorbance can be determined by operating, for each wave number, an infrared radiation absorbance to the comparative sample (absorbance corresponding to wave number $h$)$A'$=$-\log(A/BL)$     (1) and an infrared radiation absorbance to the test sample (absorbance corresponding to wave number $h$)$B'$=$-\log(B/BL)$     (2), on the assumption that the Planck value corresponding to wave number h (intensity at wave number h of the infrared radiation illuminated) is BL, the intensity at wave number h of the infrared radiation reflected from the comparative sample is A and the intensity at wave number h of the infrared radiation reflected from the test sample is B.

FIG. 1 is a spectrum chart showing an absorbance calculated. In the figure, the abscissa represents a wave number of infrared radiation while the coordinate an absorbance of infrared radiation.

As shown in the figure, observed is a difference between the absorbance of infrared radiation to the comparative sample and the absorbance of infrared radiation to the test sample.

Then, considerations were made on the difference. Specifically, differences were operated as to A' and B' corresponding respectively to the wave numbers determined by (1) and (2), according to equation (11). The difference, hereinafter is referred to as "absorbance difference".

$$\text{Absorbance difference} = B' - A' \tag{11}$$

Namely, the absorbance difference referred here is obtained by subtracting the infrared radiation absorbance of the comparative sample from the infrared radiation absorbance of the test sample, which is indicative of a difference between the infrared radiation absorbance of the test sample and the infrared radiation absorbance of the comparative sample.

Figure 3:
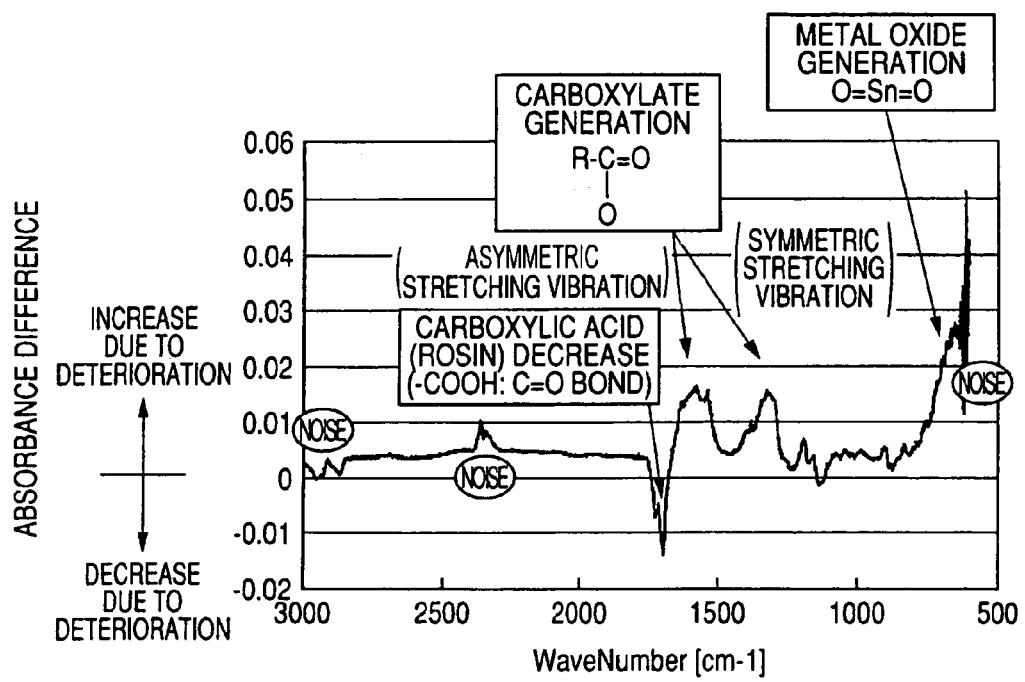
FIG. 3 is a chart showing an absorbance difference obtained by subtracting an infrared radiation absorbance of comparative-sample solder material from an infrared radiation absorbance of test-sample solder material.

FIG. 3 is a chart showing a relationship between a wave number of infrared radiation and an absorbance difference corresponding to the wave number. Namely, the FIG. 3 chart shows an absorbance difference that is a subtraction of an absorbance of the comparative sample from an absorbance of the test sample.

From FIG. 3, it can be known that there is a great difference between the comparative sample and the test sample, with respect to the absorbance at around 600 $cm^{-1}$, 1300 $cm^{-1}$, 1600 $cm^{-1}$ and 1700 $cm^{-1}$.

Specifically, it can be known that the infrared radiation absorbance of the test sample is higher than the infrared radiation absorbance of the comparative sample, at around 600 $cm^{-1}$, 1300 $cm^{-1}$ and 1600 $cm^{-1}$. It can be also known that the infrared radiation absorbance of the test sample is lower than the infrared radiation absorbance of the comparative sample, at around 1700 $cm^{-1}$.

It is known that, on the infrared radiation spectrum chart, the absorption observed at around 600 $cm^{-1}$ is due to the vibration based on an oxygen-metal bond of a metal oxide. The absorption observed at around 1300 $cm^{-1}$ is known to be due to the symmetric stretching vibration based on carboxylic acid while the absorption observed at around 1600 $cm^{-1}$ is known due to the asymmetric stretching vibration based on carboxylate. Furthermore, the absorption observed at around 1700 $cm^{-1}$ is known to show an absorption due to the stretching vibration based on double-bond in carboxylic acid.

From the fact that the infrared radiation absorbance at around 600 $cm^{-1}$ is higher for the test sample than for the comparative sample, it can be understood that the test sample contains metal oxide in a greater amount and higher in oxidation degree than the comparative sample.

Moreover, from the fact that the infrared radiation absorbance at around 1300 $cm^{-1}$ and 1600 $cm^{-1}$ is higher for the test sample than for the comparative sample, it can be understood that the test sample contains carboxylate greater in amount and higher in viscosity than the comparative sample.

Furthermore, from the fact that the infrared radiation absorbance at around 1700 $cm^{-1}$ is lower for the test sample than for the comparative sample, it can be understood that the test sample contains a lower amount of carboxylic acid less and is lower in reducing power than the comparative sample.

In this manner, this example determines, for each wave number of the infrared radiation spectrum, an infrared radiation absorbance for the test-sample cream solder (first infrared radiation absorbance) and an infrared radiation absorbance for the comparative-sample cream solder (second infrared radiation absorbance), respectively from an intensity of an infrared radiation reflected from the test-sample cream solder (intensity from test sample) and an intensity of an infrared radiation reflected from the comparative-sample cream solder (intensity from comparative sample).

Then, for each wave number of infrared radiation spectrum, an absorbance difference is determined that is a subtraction of an absorbance of the comparative-sample cream solder from an absorbance of the test-sample cream solder. By referring to the absorbance difference of at around 600 $cm^{-1}$, 1300 $cm^{-1}$, 1600 $cm^{-1}$ and 1700 $cm^{-1}$, it is possible to determine comparatively the content of metal oxide, carboxylic and carboxylate in the test-sample cream solder relative to that in the comparative-sample cream solder.

From the metal oxide content, it is possible to determine comparatively the oxidation degree of the test-sample cream solder. From the carboxylic-acid content, it is possible to determine comparatively the reducing power of the test-sample cream solder. From the carboxylate content, it is possible to determine comparatively the viscosity of the test-sample cream solder.

Figures 4A, 4B:
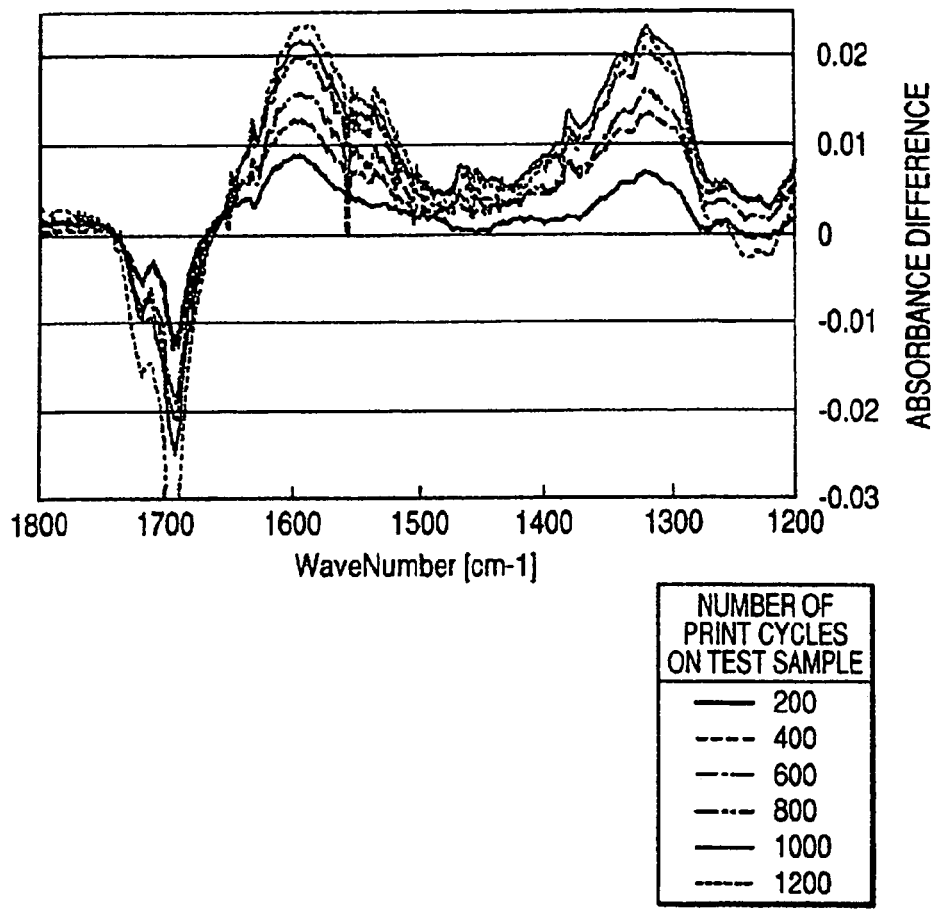

FIG. 4A shows a result of an analysis conducted on a cream solder taken in a new-product state as a comparative sample and cream solders, printed in the number of cycles of 200, 400, 600, 800, 1000 and 1200 times, respectively, through the printing process to the boards, as test samples, according to the method shown in the present example.

FIG. 4A is a chart showing, for each test sample, a relationship between an infrared radiation wave number and an absorbance difference obtained by subtracting an absorbance of the comparative-sample cream solder from an absorbance of a test-sample cream solder corresponding to the wave number. The abscissa represents an infrared radiation wave number while the ordinate represents an absorbance difference that is a difference in absorbance between the comparative-sample cream solder and the test-sample cream solder.

From FIG. 4A, it can be seen that the absorbance increases at around 1300 $cm^{-1}$ and 1600 $cm^{-1}$ with the increasing number of print cycles of cream solder whereas the absorbance is decreased at around 1700 $cm^{-1}$. From this fact, it can be understood that, in the cream solder, the carboxylic acid decreases and the carboxylate increases with the increasing number of print cycles. From the result of increasing carboxylic acid, it can be analyzed that the viscosity of the cream solder increases with the increasing number of print cycles.

When the test samples are actually measured for viscosity, it was confirmed that there is a positive correlation between the number of print cycles with cream solder and the viscosity of cream solder as shown in FIG. 4B. It was also confirmed that there is a positive correlation between the infrared radiation absorbance of the cream solder at around 1600 $cm^{-1}$ and the viscosity of the cream solder whereas there is a negative correlation between the infrared radiation absorbance of the cream solder at around 1700 $cm^{-1}$ and the viscosity of the cream solder. The reason why such relationships are held is because of the following. Namely, as the number of cream-solder-print cycles increases, the carboxylic acid contained in the cream solder decreases to decrease the infrared radiation absorbance at around 1700 $cm^{-1}$ whereas the carboxylate contained in the cream solder increases to increase the infrared radiation absorbance at around 1600 $cm^{-1}$, wherein the viscosity increases with increasing carboxylate.

The embodiment shown in the above calculated the infrared radiation absorbance of the test-sample cream solder and the infrared radiation absorbance of the comparative-sample cream solder. However, unless calculating an absorbance, it is possible to determine comparatively the content of metal oxide, carboxylic and carboxylate in the test-sample cream solder. Specifically, for each wave number of 500 $cm^{-1}$-3000 cm$^{-1}$, detected are the intensity of infrared radiation reflected the test-sample cream solder and the intensity of an infrared radiation reflected the comparative-sample cream solder. For each wave number, operation is made on each intensity detected, according to equation (21).

$$\text{Intensity difference} = B - A \tag{21}$$

A: intensity of an infrared radiation reflecting from the comparative sample.

B: intensity of an infrared radiation reflecting from the test sample.

Here, "intensity difference" is a subtraction of the infrared radiation intensity detected of the comparative sample from the infrared radiation intensity detected of the test sample, i.e. a difference between the infrared radiation intensity detected of the test sample and the infrared radiation intensity detected of the comparative sample.

By referring to the absorbance difference at 600 cm$^{-1}$, 1300 cm$^{-1}$, 1600 cm$^{-1}$ and 1700 cm$^{-1}$, it is possible to determine the difference in infrared radiation absorption based on the metal oxide, carboxylic and carboxylate of the test-sample cream solder, relative to the comparative-sample cream solder. For this reason, it is possible to determine the content of metal oxide, carboxylic and carboxylate in the test-sample cream solder, relative to the comparative-sample cream solder.

Meanwhile, by using a ratio in absorbance or in intensity instead of the absorbance or intensity difference, it is possible to determine the difference in infrared radiation absorbance between the comparative and test samples, and hence to comparatively determine the content of metal oxide, carboxylic and carboxylate in the test-sample cream solder.

For example, for each wave number, the intensity ratio may be determined that is a ratio of the infrared radiation intensity detected of the test sample and the infrared radiation intensity detected of the comparative sample, according to the following operation.

$$\text{Intensity ratio} = B/A \tag{31}$$

For each wave number, the absorbance ratio may be determined that is a ratio of an infrared radiation absorbance of the test sample and an infrared radiation absorbance of the comparative sample, according to the following operation.

$$\text{Absorbance ratio} = B'/A' \tag{41}$$

A': infrared radiation absorbance of the comparative sample.

B': infrared radiation absorbance of the test sample. According to the examples shown above, infrared radiation intensity detection is required for each wave number of 5000-3000 cm$^{-1}$ for the cream solders of the comparative and test samples, to calculate an infrared radiation absorbance difference, absorbance ratio, intensity difference or intensity ratio. Alternatively, the procedure may be taken to detect the intensity only at a particular wave number of infrared radiation, to calculate an absorbance, absorbance difference, intensity ratio, intensity difference or intensity ratio as to the particular wave number. The particular wave number means a wave number where infrared radiation absorption is recognized based on at least one of metal oxide, carboxylic acid and carboxylate. In this example, it is at least one of 600 cm$^{-1}$, 1300 cm$^{-1}$, 1600 cm$^{-1}$ and 1700 cm$^{-1}$.

Meanwhile, the light illuminated from the floodlight 15 is non-uniform in intensity. Even where an infrared radiation is illuminated to the comparative and test samples by using the same floodlight 15, if infrared radiation illumination is different in timing, there occurs as a slight difference between the intensity of infrared radiation illuminated to the comparative sample and the intensity of infrared radiation illuminated to the test sample. Such a difference may have a bad effect upon the intensity of infrared radiation reflecting from the cream solder.

For this reason, correction is preferably made in determining an intensity difference, intensity ratio, absorbance difference or absorbance ratio at a particular wave number. Below, explanation is made on a procedure to determine a corrected one of intensity difference, intensity ratio, absorbance difference or absorbance ratio.

At first, a solder-material test apparatus 1 is set with a reference wave number outside the wave number band, where infrared radiation absorption based on a metal oxide, carboxylic acid and carboxylate is observed, at which wave number there is no difference in reflected infrared radiation intensity between the comparative and test samples.

Then, detected are the intensity at the reference wave number of infrared radiation reflected from comparative sample and the intensity at the reference wave number of infrared radiation reflected from the test sample. Furthermore, detected are an intensity at the particular wave number of infrared radiation reflected upon the comparative sample and the intensity at the particular wave number of infrared radiation reflected from the test sample.

Here, it is assumed that the intensity at the reference wave number of infrared radiation reflected from the comparative sample (comparative-sample reference intensity) is $A_{ref}$, the intensity at the reference wave number of infrared radiation reflected from the test sample (test-sample reference intensity) is $B_{ref}$, the intensity at the particular wave number of infrared radiation reflected from the comparative sample (comparative-sample intensity) is $A_{tar}$ and the intensity at the particular wave number of infrared radiation reflected from the test sample (test-sample intensity) is $B_{tar}$.

Meanwhile, it is assumed that the infrared radiation absorbance at the reference wave number of the comparative sample (fourth infrared radiation absorbance) is $A'_{ref}$, the infrared radiation absorbance at the reference wave number of the test sample (third infrared radiation absorbance) is $B'_{ref}$, the infrared radiation absorbance at the particular wave number to comparative sample (second infrared radiation absorbance) is $A'_{tar}$ and the infrared radiation absorbance at the particular wave number of the test sample (first infrared radiation absorbance) is $B'_{tar}$.

The absorbances are calculated according to the similar technique to equations (1), (2). Namely, it can be determined by the following provided that the intensity corresponding to a reference wave number of infrared radiation to be illuminated to the comparative sample is $BL_{ref}$ and the intensity corresponding to a particular wave number of infrared radiation to be illuminated to the test sample is $BL_{tar}$.

$$A'_{ref} = -\log(A_{ref}/BL_{ref}) \tag{61}$$

$$B'_{ref} = -\log(B_{ref}/BL_{ref}) \tag{62}$$

$$A'_{tar} = -\log(A_{tar}/BL_{tar}) \tag{63}$$

$$B'_{tar} = -\log(B_{tar}/BL_{tar}) \tag{64}$$

Then, corrected intensity difference, corrected intensity ratio, corrected absorbance difference and corrected absorbance ratio can be determined by the following.

$$\text{Corrected intensity difference} = (B_{tar} - B_{ref}) - (A_{tar} - A_{ref}) \tag{71}$$

$$\text{Corrected intensity ratio} = (B_{tar} - B_{ref})/(A_{tar} - A_{ref}) \tag{72}$$

Corrected absorbance difference=$(B'_{tar}-B'_{ref})-(A'_{tar}-A'_{ref})$ (73)

Corrected absorbance difference=$(B'_{tar}-B'_{ref})/(A'_{tar}-A'_{ref})$ (74)

Due to this, even when there is a slight difference between the intensity of infrared radiation to be illuminated to the comparative sample and the intensity of infrared radiation to be illuminated to the test sample, it is possible to determine a corrected intensity difference, corrected intensity ratio, corrected absorbance difference and corrected absorbance ratio with such a difference nearly eliminated because the intensities and absorbance are each subtracted by an intensity at the reference wave number corresponding to the difference.

Corrected intensity difference, corrected intensity ratio, corrected absorbance difference and corrected absorbance ratio can be determined by the following.

Corrected intensity difference=$(B_{tar} \times A_{ref}/B_{ref})-A_{tar}$ (75)

Corrected intensity ratio=$(B_{tar} \times A_{ref}/B_{ref})/A_{tar}$ (76)

Corrected absorbance difference=$(B'_{tar} \times A'_{ref}/B'_{ref})-A'_{tar}$ (77)

Corrected absorbance ratio=$(B'_{tar} \times A'_{ref}/B'_{ref})/A'_{tar}$ (78)

This method uses $A_{ref}/B_{ref}$ or $A'_{ref}/B'_{ref}$ as a correction coefficient for the difference.

Meanwhile, the particular wave numbers (600 cm$^{-1}$, 1300 cm$^{-1}$, 1600 cm$^{-1}$, 1700 cm$^{-1}$) can be changed in value. Namely, the particular wave numbers are not limited to 600 cm$^{-1}$, 1300 cm$^{-1}$, 1600 cm$^{-1}$, 1700 cm$^{-1}$, but effective ranges can be established for particular wave numbers. This point is detailed.

At first, by taking a solder material in a new product state as a comparative sample and solder materials printed the number of cycles of 200, 400, 600, 800, 1000 and 1200 through the printing process as test samples, the absorbance differences were determined for the test samples according to the method shown in the example. The result is shown in FIGS. 5 to 8. FIG. 5 shows the absorbance differences at a wave number band of 520 cm$^{-1}$-700 cm$^{-1}$, FIG. 6 the absorbance differences at a wave number band of 1270 cm$^{-1}$-1430 cm$^{-1}$, FIG. 7 the absorbance differences at a wave number band of 1500 cm$^{-1}$-1650 cm$^{-1}$, and FIG. 8 the absorbance differences at a wave number band of 1665 cm$^{-1}$-1730 cm$^{-1}$.

The metal oxide (tin dioxide) contained in the solder material has an absorption peak to be detected at around 600 cm$^{-1}$. However, as shown in FIG. 5, if detecting at 520 cm$^{-1}$-700 cm$^{-1}$, the absorption differences can be distinguished in differences between the test samples. If detecting at 557-613 cm$^{-1}$, the absorption differences can be observed more conspicuously in difference between the test samples. Consequently, by taking at least any one of wave numbers lying between 520 cm$^{-1}$-700 cm$^{-1}$ as a particular wave number, metal oxide content can be analyzed on the test sample.

Meanwhile, the symmetric stretching vibration based on carboxylic acid has an absorption peak to be detected at around 1300 cm$^{-1}$ (exactly 1323 cm$^{-1}$). However, as shown in FIG. 6, If detecting at 1270 cm$^{-1}$-1430 cm$^{-1}$, the absorption differences can be distinguished in difference between the test samples. If detecting at 1282 cm$^{-1}$-1382 cm$^{-1}$, the absorption differences can be observed more conspicuously in difference between the test samples. Consequently, by taking at least any one of wave numbers lying between 1270 cm$^{-1}$-1430 cm$^{-1}$ as a detected wave number, carboxylate content can be analyzed as to the sample.

Figure 7:
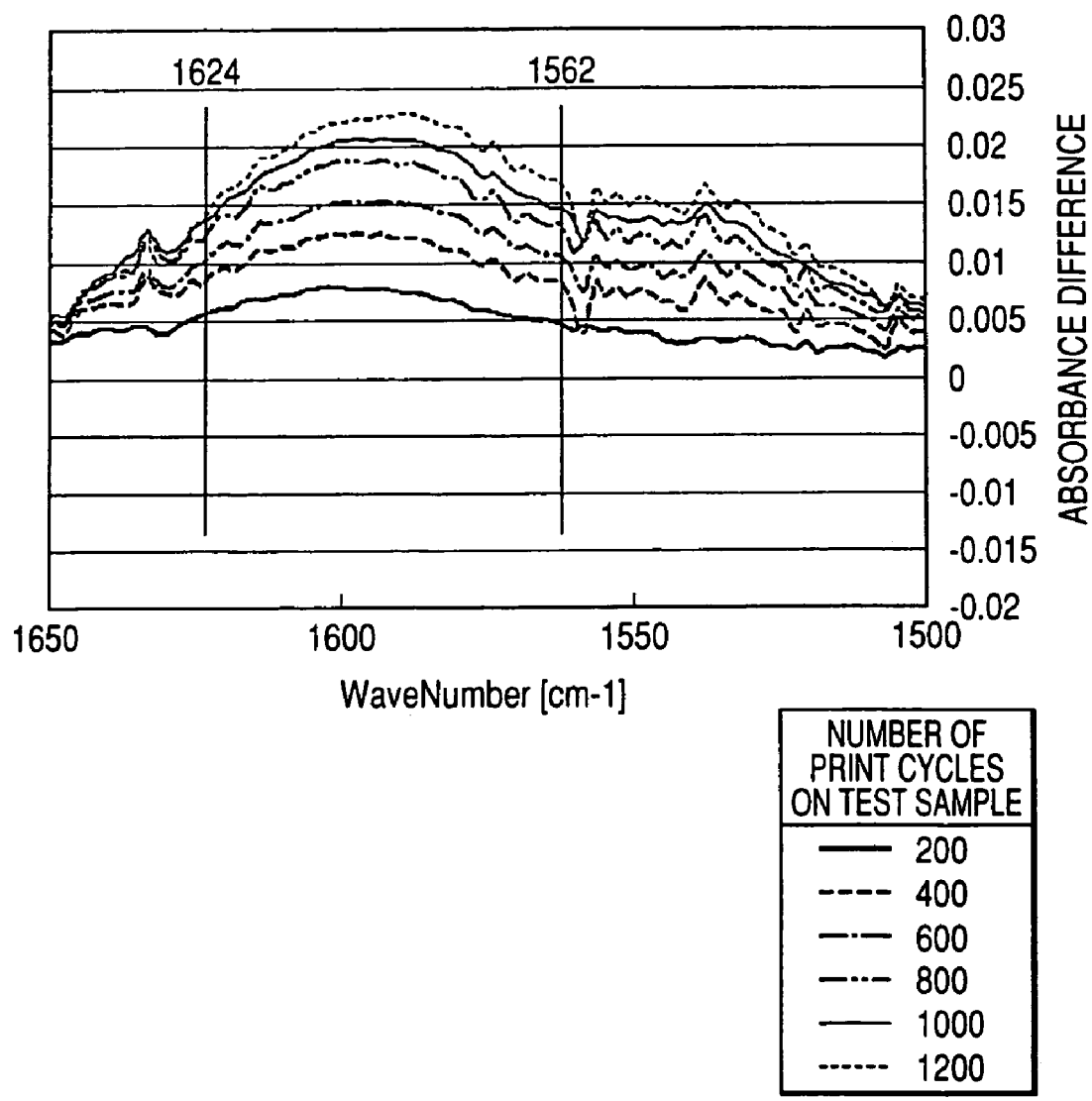
FIG. 7 is a chart showing, for each test sample, the absorbance differences, as to a plurality of test samples, obtained by subtracting infrared radiation absorbance to comparative-sample solder material from infrared radiation absorbance to test-sample solder material, in a wave-number band of 1500 $cm^{-1}$-1650 $cm^{-1}$.

The assymetric stretching vibration based on carboxylate has an absorption peak to be detected at around 1600 cm$^{-1}$ (exactly 1590 cm$^{-1}$). However, as shown in FIG. 7, If detecting at 1500 cm$^{-1}$-1650 cm$^{-1}$, the absorption differences can be distinguished in difference between the test samples. If detecting at 1562 cm$^{-1}$-1624 cm$^{-1}$, the absorption differences can be observed more conspicuously in differences between the test samples. Consequently, by taking at least any one of wave numbers lying between 1500 cm$^{-1}$-1650 cm$^{-1}$ as a wave number for detection, carboxylate content can be analyzed on the test sample.

Figure 8:
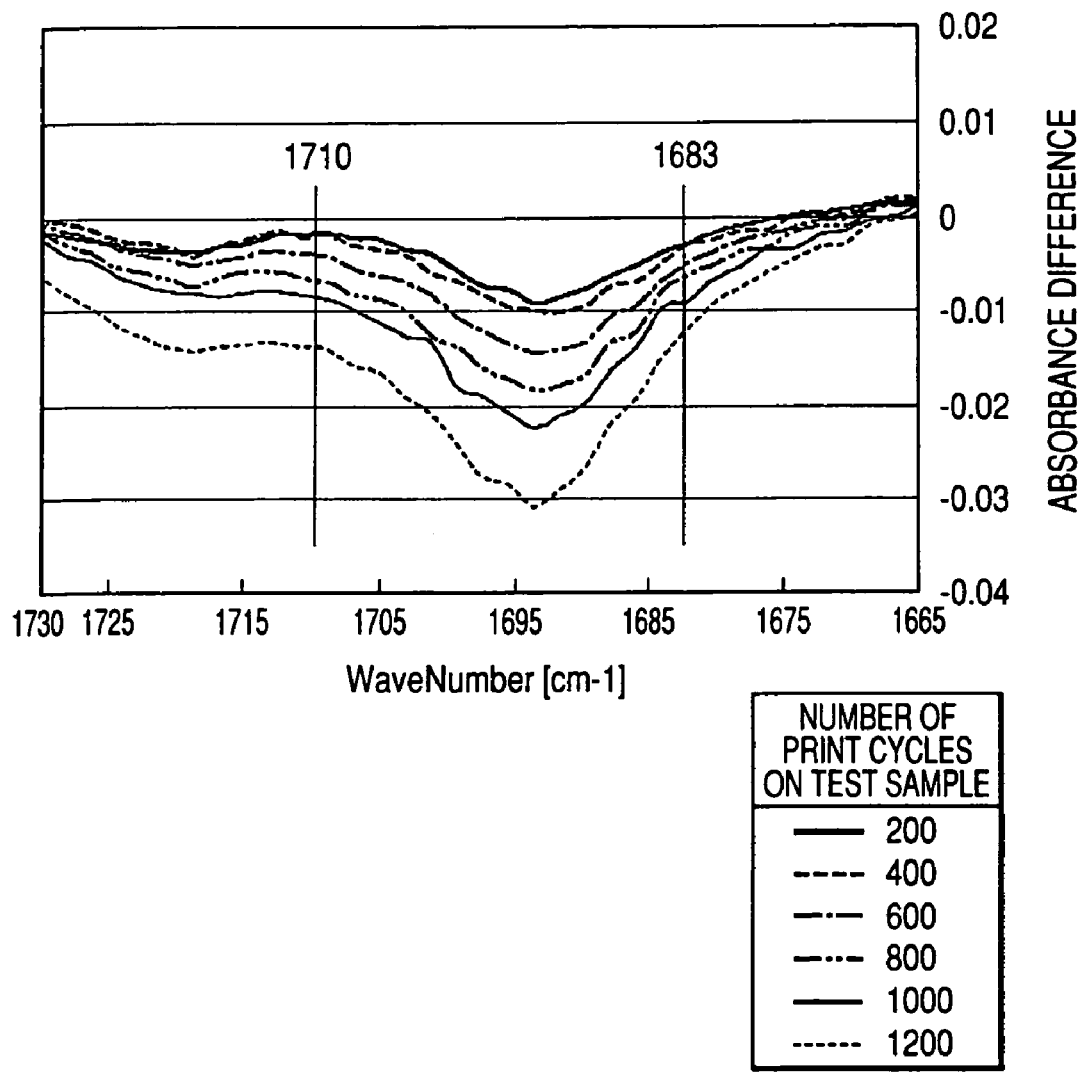
FIG. 8 is a chart showing, for each test sample, the absorbance differences, as to a plurality of test samples, obtained by subtracting infrared radiation absorbance to comparative-sample solder material from infrared radiation absorbance to test-sample solder material, in a wave-number band of 1665 $cm^{-1}$-1725 $cm^{-1}$.

Furthermore, the carbon-oxygen double bond of carboxylate has an absorption peak to be detected at around 1700 cm$^{-1}$ (exactly 1590 cm$^{-1}$). However, as shown in FIG. 8, If detecting at 1665 cm$^{-1}$-1730 cm$^{-1}$, the absorption differences can be distinguished in differences between the test samples. If detecting at 1683 cm$^{-1}$-1710 cm$^{-1}$, the absorption differences can be observed more conspicuously in differences between the test samples. Consequently, by taking at least any one of wave numbers lying between 1665 cm$^{-1}$-1730 cm$^{-1}$ as a wave number for detection, carboxylic acid content can be analyzed on the test sample.

Solder Material Test Apparatus

Now described is a solder material test apparatus that realizes the solder material test method in the embodiment. Note that the solder material test apparatus, described below, is a mere exemplification of the apparatus that realizes the solder material test method in the embodiment, i.e. the solder material test apparatus described below is not necessarily needed in realizing the solder material test method in the embodiment.

The solder material test apparatus in this embodiment includes a light source that illuminates light to the test-sample and comparative-sample solder materials, intensity detecting means that detects a first intensity at a particular wave number of infrared radiation reflected from the test-sample solder material due to the light illumination and a second intensity at the particular wave number of infrared radiation reflected from the comparative-sample solder material due to the light illumination, and control means that outputs a deterioration parameter indicative of a comparative deterioration degree of the test-sample solder material relative to the comparative-sample solder material.

Here, the deterioration parameter includes a difference between the first intensity and the second intensity and a ratio of the first intensity and the second intensity. Alternatively, by determining, from the first intensity, a first infrared radiation absorbance at the particular wave number of the test-sample solder material and, from the first intensity, a second infrared radiation absorbance at the particular wave number of the comparative-sample solder material, the deterioration parameter may be provided as a difference between the first and second infrared radiation absorbances thus obtained. Furthermore, the deterioration parameter may be by the ratio of the first infrared radiation absorbance and the second infrared radiation absorbance.

Due to this, the deterioration parameter is given indicative of a difference degree between the infrared radiation absorbance at a particular wave number of the test-sample solder material and the infrared radiation absorbance at a particular wave number of the comparative-sample solder material. Here, depending upon the content of metal oxide, carboxylic acid and carboxylate in the solder material, the infrared radiation absorbance at a particular wave number of solder material changes to change the intensity of an infrared radiation at the particular wave number reflected from the solder material.

Accordingly, by referring to the deterioration parameter, the operator at the solder material test apparatus is allowed to know the content of metal oxide, carboxylic acid and carboxylate in the test-sample solder material. Thus, he/she can conduct a test on a test-sample solder material for relative deterioration degree.

In case an infrared radiation-transmissive optical filter is provided between the light source and the solder material or between the solder material and the intensity detecting means in the above arrangement, the intensity detecting means is allowed to detect infrared radiation reflected from the solder material.

Now description is made on an example of the solder material test apparatus in the present embodiment.

EXAMPLE 2

Figure 9:
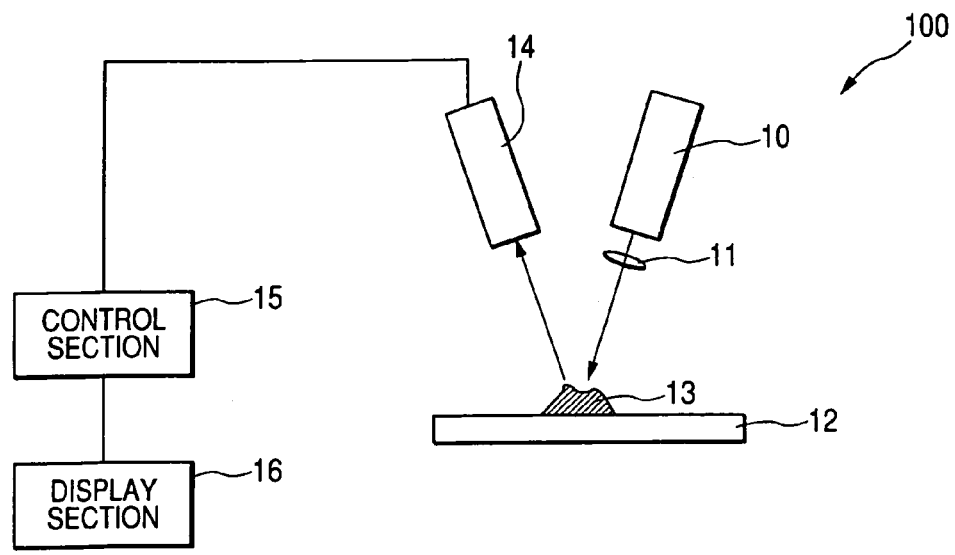
FIG. 9 is a typical view showing a solder material test apparatus that realizes the solder material test method in the example of the invention.

A solder material test apparatus 100 in this example has a light source 10, a band-pass filter 11, a plate 12, a solder material 13, a photoelectric converter (intensity detecting means) 14, a control section (control means) 15 and a display section (display means) 16, as shown in FIG. 9.

The light source 10 is a lamp that illuminates light toward the plate 12, which employs, say, a ceramic light source.

The band-pass filter 11 is an optical filter arranged on the optical axis of the light source 10, at between the light source 10 and the plate 12. The band-pass filter 11 transmits an infrared radiation at a particular wave number only. The particular wave number is similar to the explanation in example 1, at which wave number infrared radiation absorption is recognized due to at least one of metal oxide, carboxylic acid and carboxylate.

The plate 12 is a stage on which a solder material 13 is to be placed. The light from the light source 10 is illuminated to the solder material 13 rested on the plate 12 through the band-pass filter 11. Accordingly, the light illuminated to the solder material 13 is of infrared radiation at a particular wave number.

The solder material 13 is relevant to the foregoing comparative-sample or test-sample solder material, which is reflective of the light illuminated.

The photoelectric converter 14 is to detect the intensity of incoming infrared radiation. The photoelectric converter 14 generates an analog signal indicative of the detected intensity of infrared radiation and forwards the analog signal to the control section 15. The photoelectric converter 14 is, for example, a device using MCT (photoconductor, HgCdTe). The photoelectric converter 14 is arranged in a position axial of infrared radiation reflected from the solder material 13 on the plate 12.

The control section 15 is a block for processing the analog signal sent from the photoelectric converter 14, which is configured with an A/D (analog to digital) converter that converts an analog signal into a digital signal, and a computer that performs a data processing depending upon the digital signal.

The display section 16 is a display panel that displays an image based on the image data sent from the control section 15.

According to the solder material test apparatus 100, the digital signal processed by the computer of the control section 15 provides data indicative of the intensity at a chosen wave number of the infrared radiation reflected from the solder material 13.

In the solder material test apparatus 100, a comparative-sample solder material 13 is placed on the plate 12. By illuminating infrared radiation at a particular wave number to the solder material 13, the photoelectric converter 14 is caused to detect the intensity of infrared radiation (second intensity) reflected from the comparative-sample solder material 13. Thereafter, a test-sample solder material 13 is put on the plate 12, to detect the intensity of infrared radiation (first intensity) by a similar operation. Due to this, the control section 15 is delivered with the data indicative of the intensity of infrared radiation reflected the comparative-sample solder material 13 and the data indicative of the intensity of infrared radiation reflected the test-sample solder material 13, in order.

Depending upon the intensities, the control section 15 determines infrared radiation absorbance at a particular wave number of the test sample (first infrared radiation absorbance) and infrared radiation absorbance at a particular wave number of the comparative sample (second infrared radiation absorbance). The control section 15 further determines an absorbance difference, a subtraction of the infrared radiation absorbance at a wave number considered of the test sample from the infrared radiation absorbance at a wave number considered of the comparative sample. The display section 16 is caused to display an image representative of the absorbance difference. This allows the operator at the solder material test apparatus 100 to analyze the test sample for at least one of metal-oxide relative content, carboxylic acid relative content and carboxylate relative content, and hence the relative deterioration degree of the test-sample solder material.

Alternatively, the control section 15 may be configured to output any of (a) an absorbance ratio that is a ratio of an infrared radiation absorbance at a particular wave number of the sample and an infrared radiation absorbance at a particular wave number of the comparative sample, (b) an intensity difference that is a subtraction of an intensity of infrared radiation at a particular wave number reflected from the test sample from an intensity of infrared radiation at a particular wave number reflected from the comparative sample, and (c) an intensity ratio that is a ratio of an intensity of infrared radiation at a particular wave number reflected from the test sample to an intensity of infrared radiation at a particular wave number reflected from the comparative sample. Namely, it may be configured to operate any one of equations (21), (31) and (41) and output the result thereof.

Figure 10:
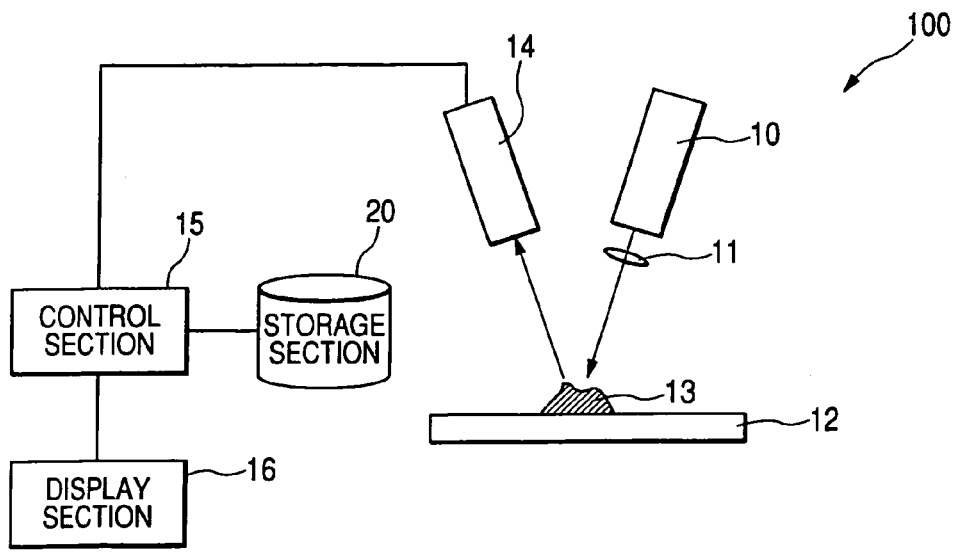
FIG. 10 is a typical view showing a modification to the solder material test apparatus shown in FIG. 9.

In the solder material test apparatus 100, the control section 15 may be connected with a storage section 20, as shown in FIG. 10. This arrangement can previously detect only the intensity of infrared radiation reflected the comparative-sample solder material and store data indicative of the intensity in the storage section 20. This satisfactorily requires to once detect the intensity of infrared radiation reflected from the comparative-sample solder material even where tests must be made successively on a plurality of test samples.

Figure 11:
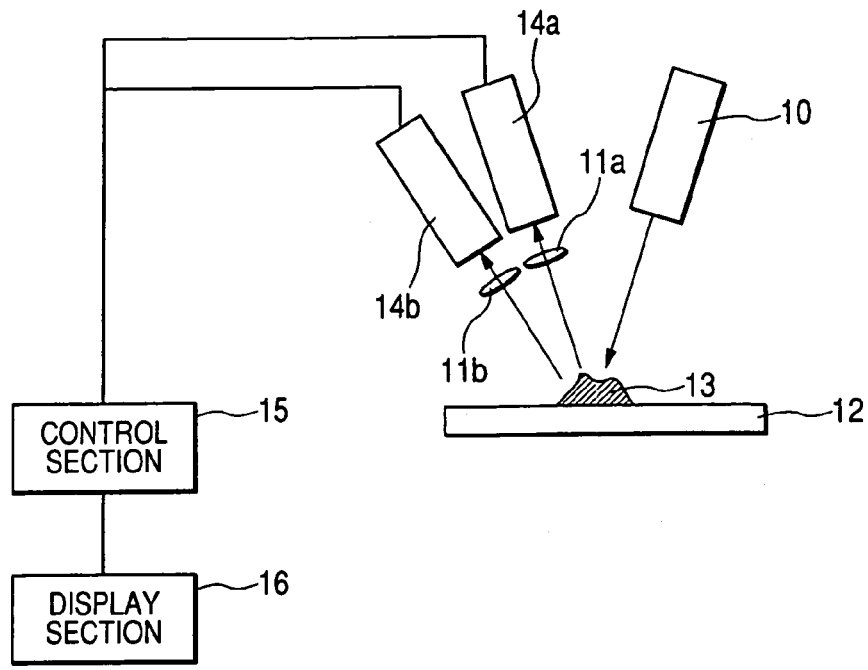
FIG. 11 is a typical view showing another modification to the solder material test apparatus shown in FIG. 9.

Instead of the arrangement of the band-pass filter 11 between the light source 10 and the plate 12, the band-pass filter 11 may be provided, between the solder material 13 on the plate 12 and the photoelectric converter 14, on the optical axis of the light reflected from the solder material 13, as shown in FIG. 11.

As shown in FIG. 11, the photoelectric converter 14 and band-pass filter 11 may both be provided in plurality. With this arrangement, provided that the particular wave number of the band-pass-filter 11a is provided with a wave number to absorb infrared radiation due to metal oxide while the particular wave number of the band-pass-filter 11b is provided with a wave number to absorb infrared radiation due to carboxylic acid, the test sample can be analyzed for metal-oxide content and carboxylic-acid content.

Figure 12:
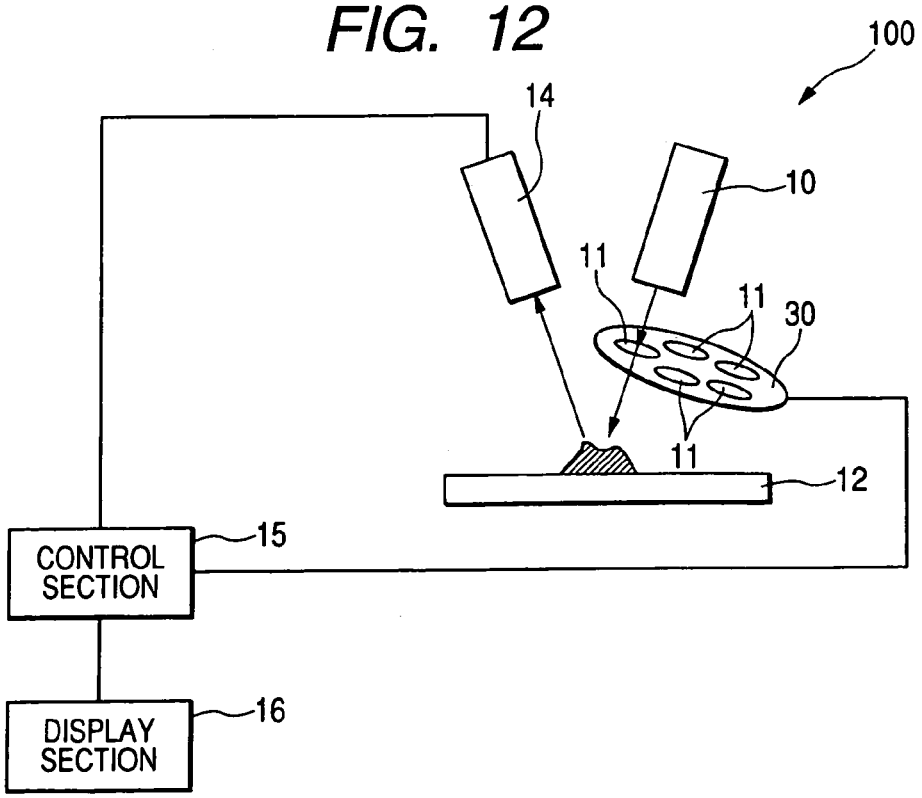
FIG. 12 is a typical view showing further modification to the solder material test apparatus shown in FIG. 9.

As shown in FIG. 12, a rotary member 30 including a plurality of band-pass filters 11 may be provided on the optical axis of the light source 10, between the light source 10 and the plate 12. The rotary member 30 is arranged to place any one of the band-pass filters 11 onto the optical axis of the light source 10, and to rotate depending upon the command from the control section 15, thus changing over the band-pass filter 11 placed on the axis.

In this arrangement, by providing the band-pass filters 11 of the rotary member 30 respectively with different particular wave numbers, it is possible to detect infrared radiation at a different wave number reflected from the solder material 13. This makes it possible to analyze the test-sample solder material 13 for metal-oxide content, carboxylic-acid content and carboxylate content by one test operation.

Meanwhile, each band-pass filter 11 of the rotary member 30 may include an optical filter, that transmits infrared radiation at a reference wave number, explained in example 1. The photoelectric converter 14 is caused to detect the intensity at the reference wave number of the infrared radiation reflected from the comparative sample (fourth intensity) and the intensity at the reference wave number of the infrared radiation reflected from the test sample (third intensity). Furthermore, by causing the control section 15 to operate equations (61)-(64) and (71)-(78) explained in example 1, it is possible to output corrected intensity difference, intensity ratio, absorbance difference and absorbance ratio.

Figure 13:
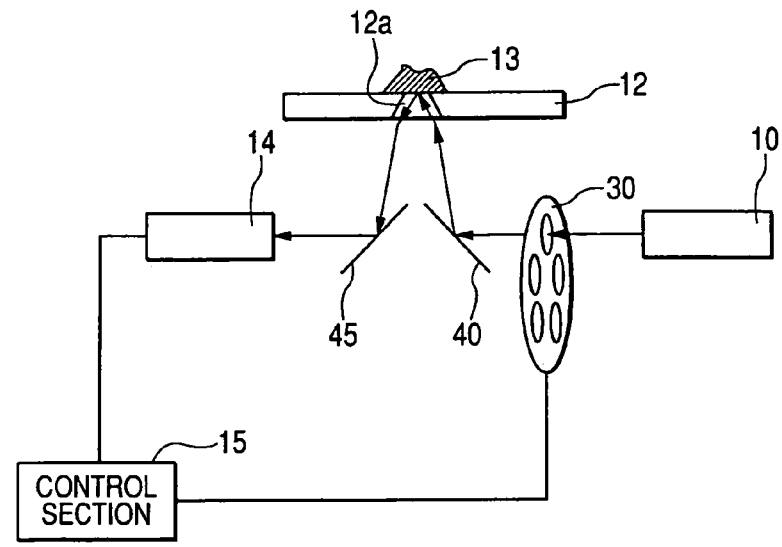
FIG. 13 is a typical view showing an arrangement further modified the solder material test apparatus shown in FIG. 12.

The arrangement can be made as shown in FIG. 13.

In a FIG. 13 solder material test apparatus 100, the plate 12 includes a light-transmissive region (ZnSe, or the like) 12a where light is allowed to transmit through the both surfaces. A solder material 13 is placed on the light-transmissive region 12a at one surface of the plate 12.

A light source 10, a rotary member 30 and a photoelectric converter 14 are arranged in positions opposed to the other surface of the plate 12, wherein mirrors 40, 45 are arranged. Specifically, the rotary member 30 and the mirror 40 are arranged in this order on the optical axis of the light source 10, in a direction along the light traveling from the light source 10. The mirror 40 is arranged to reflect the light, illuminated from the light source 10 through the rotary member 30, into a direction toward the light-transmissive region 12a. Furthermore, the mirror 45 is arranged to reflect the light, from the light-transmissive region 12a, into a direction toward the photoelectric converter 14.

According to this arrangement, the band-pass filter 11 included in the rotary member 30 permits only infrared radiation at a chosen wave number of the light emitted from the light source 10. The transmitted infrared radiation is guided to the mirror 40. The infrared radiation is reflected upon the mirror 40 and guided to the light-transmissive region 12a, to reach the solder material 13 through the light-transmissive region 12a. The infrared radiation reaching the solder material 13 is reflected thereupon and guided to the mirror 45 through the light-transmissive region 12a. The infrared radiation guided to the mirror 45 reflects upon the mirror 45 and enters the photoelectric converter 14. Due to this, the photoelectric converter 14 is allowed to detect the intensity of the infrared radiation reflected the solder material 13.

Meanwhile, the solder material test apparatus 100 shown in FIG. 12 can be modified for in-line analysis application. For example, a solder material test apparatus 100 shown in FIG. 14 is for in-line analysis application, i.e. for the purpose of in-line-analyzing the deterioration degree of a solder material being used in a printing process on a printed-circuit-board production line.

Figure 14:
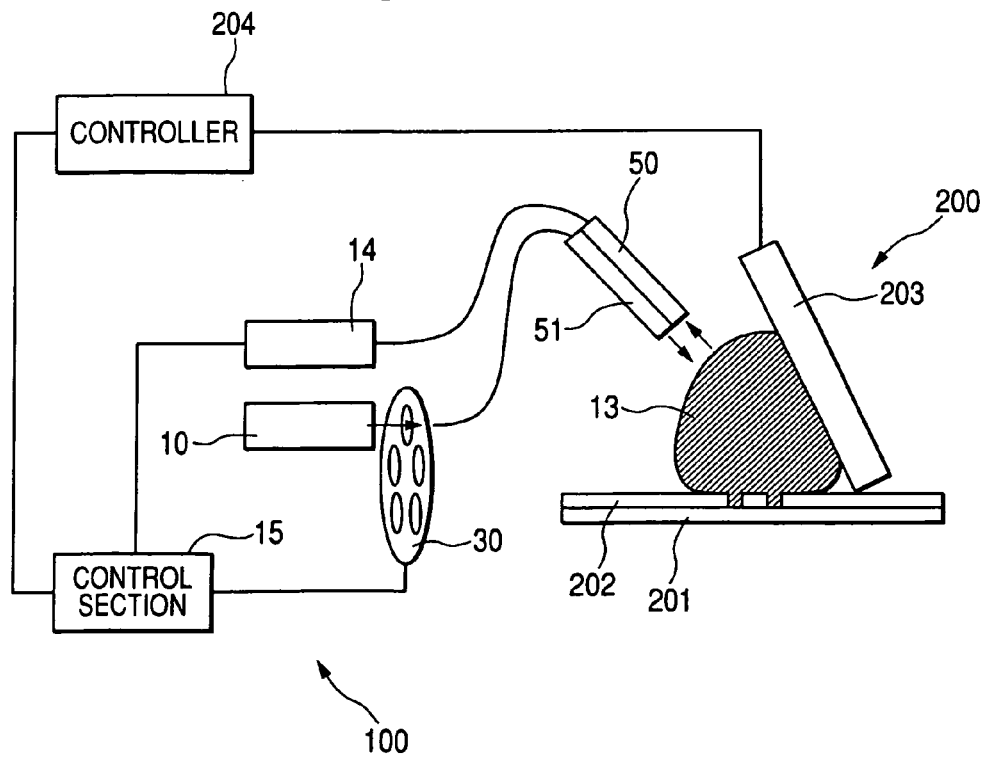
FIG. 14 is a typical view showing an arrangement modified, for in-line-analysis use, the solder material test apparatus shown in FIG. 12.

In FIG. 14, a solder material test apparatus 100 is provided close to a printer 200 for a printed board.

The printer 200 includes a board 201 printed with a solder material, a metal mask 202 arranged on the board 201 and cut with a wiring pattern, a solder material 13 placed on the metal mask 202, a squeegee 203 for moving the solder material 13 while pushing it, and a controller 204 for drive-controlling the squeegee 203.

In the solder material test apparatus 100, there are provided an optical fiber 51 for guiding the infrared radiation transmitting through the band-pass filter 11 of the rotary member 30, and an optical fiber 50 for guiding the infrared radiation reflected from the solder material 13 to the photoelectric converter 14.

According to this arrangement, the infrared light exiting the light source 10 and transmitted through the rotary member 30 is illuminated to the solder material 13 on the printer 200 through the optical fiber 51. The infrared light is reflected by the solder material 13 and guided to the photoelectric converter 14 through the optical fiber 50. Due to this, the solder material test apparatus 100 is allowed to measure the solder material 13, as a sample, for the intensity of infrared radiation reflected from the solder material 13 or infrared radiation absorbance to same, and hence to analyze, in-line, the solder material 13 for deterioration degree.

Figure 15:
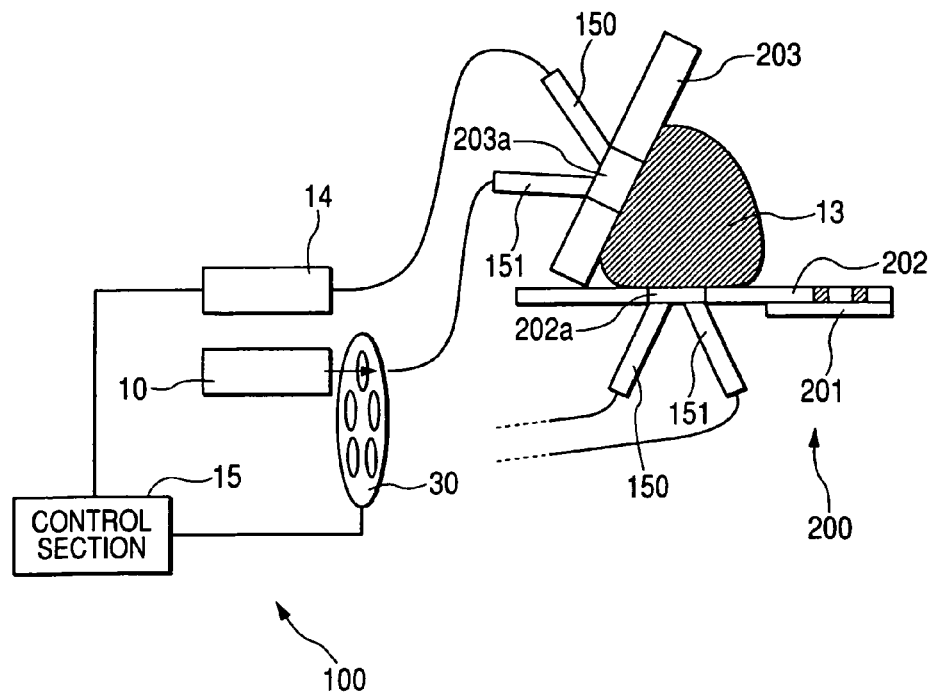
FIG. 15 is a typical view showing an arrangement modified the solder material test apparatus shown in FIG. 14.

Meanwhile, the solder material test apparatus 100 and printer 200 shown in FIG. 14 can be modified as in FIG. 15.

In the printer shown in FIG. 15, the squeegee 203 is formed with a light-transmissive region (ZnSe or the like) 203a where light is allowed to transmit through both surfaces. A solder material 13 is placed on one side of the squeegee 203.

In the solder material test apparatus 100, there are provided optical fibers 150, 151. The optical fiber 151 is to input therein the infrared radiation transmitted through the band-pass filter 11 of the rotary member 30 and allows the infrared radiation to exit onto the light-transmissive region 203a at its other surface of the squeegee 203. The optical fiber 150 is to input the light from the light-transmissive region 203a and guide the light to the photoelectric converter 14.

According to this arrangement, the infrared radiation exiting the light source 10 and transmitted through the rotary member 30 is illuminated onto the light-transmissive region 203a at its other surface of the squeegee 203 through the optical fiber 151. The illuminated infrared radiation reaches the solder material 13 through transmitting the light-transmissive region 203a. Furthermore, the infrared radiation reflects upon the solder material 13 and enters the optical fiber 150 through transmitting the light-transmissive region 203a. The infrared radiation entering the optical fiber 150 is guided to the photoelectric converter 14. Due to this, the solder material test apparatus 100 is allowed to measure, in-line, the solder material 13 placed on the printer 200, as a sample, for the intensity of infrared radiation reflected from the solder material 13 or infrared radiation absorbance of the same, and hence to analyze, in-line, the solder material 13 for deterioration degree.

Meanwhile, as shown in FIG. 15, a metal mask 202 may be structured with a light-transmissive region (ZnSe or the like) 202a where light is allowed to transmit through both surfaces thereof, to place a solder material 13 on one surface of the metal mask 202. In this structure, the optical fiber 151 is arranged to allow the infrared light coming from the band-pass filter 11 of the rotary member 30 to exit onto the light-transmissive region 202a at its other surface of the metal mask 202. The optical fiber 150 is arranged to allow the light from the light-transmissive region 202a at the other surface of the metal mask 202 to enter.

Figure 16:
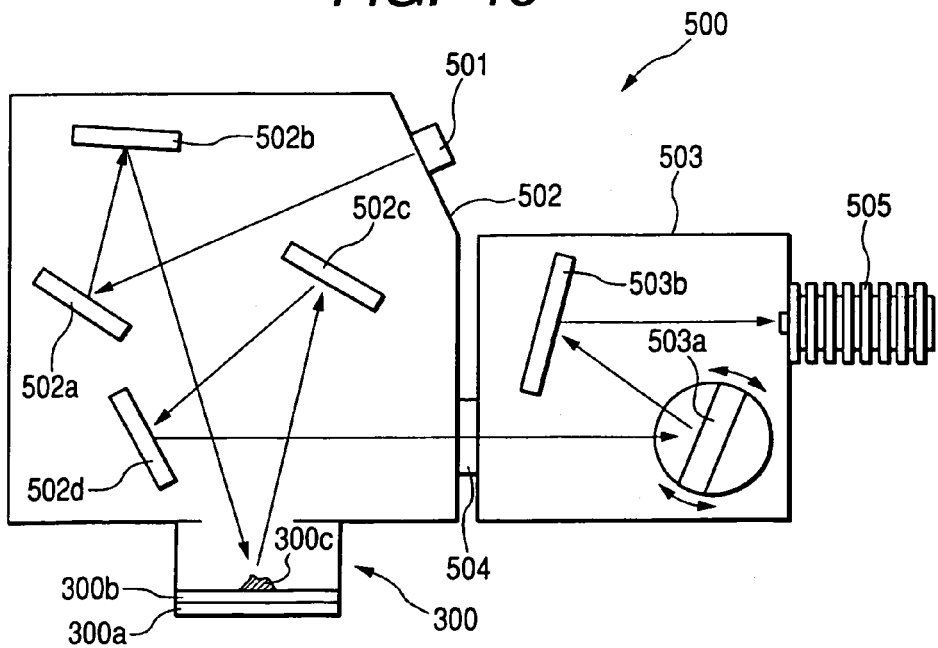
FIG. 16 is a typical view showing a solder material test apparatus in a further different form.

Although the solder material test apparatuses 100 were shown in FIGS. 12 to 15 that are capable of conducting an in-line analysis, in-line analysis can be realized by structuring a solder-material test apparatus 500 as shown in FIG. 16.

As shown in FIG. 16, a solder material test apparatus 500 is arranged adjacent a printer 300 and structurally includes a light-emitting element 501, a housing 502, a housing 503, a communication passage 504 and a light-receiving element 505.

Of the solder material test apparatus 500, the housing 502 is adjacent the printer 300, to communicate between the interiors of the housing 502 and the printer 300. Furthermore, the interiors of the housings 502, 503 communicate together by the communication passage 504.

The printer 300 is for printing a solder material on a circuit board. Within the printer 300, there is arranged a board 300a in a state where printing is being performed. A metal mask 300b is arranged on the board 300a while a solder material 300c is arranged on the metal mask.

A light-emitting element 501 is a light source to emit light to the solder material, which employs any one of a ceramic light source, a halogen lamp, an LED (light-emitting diode) and a semiconductor laser (laser diode), for example.

The housing 502 is structured with a light-introducing hole (not shown) provided adjacent the light-emitting element 501 in a manner opposing the emitting surface of the light-emitting diode 501 and for introducing the light emitted from the light emitting element 501 to the inside. Within the housing 502, there are arranged mirrors 502a, 502b, 502c and 502d.

The mirror 502a is an optical means that is arranged opposed to the emitting surface of the light-emitting surface 501 through the light-introducing hole and for receiving the light emitted from the light-emitting element 501 and reflecting the light toward the mirror 502b. The mirror 502b is an optical means that receives the light reflected by the mirror 502a and reflects the received light to the solder material 300c inside the printer 300. The mirror 502c is an optical means that receives the light reflected from the solder material 300c and reflects the received light to the mirror 502d. The mirror 502d is an optical means that receives the light reflected by the mirror 502c and reflects the received light to an interior of the housing 503 through the communication passage 504.

The light-receiving element 505 is, say, a photoelectric converter using an MCT, which is arranged on the exterior wall of the housing 503, to project its light-receiving part in the interior of the housing 503.

Within the housing 503, there are arranged a diffraction grating 503a and a mirror 503b.

The diffraction grating 503a is an element that diffracts the light reflected from the mirror 502d of the housing 502. Of the light, a particular wave number of infrared light is diffracted to the mirror 503b. The mirror 503b is an optical means that receives the infrared radiation diffracted by the diffraction grating 503a and reflects the infrared radiation to the light-receiving part of the light-receiving element 505.

According to the above arrangement, the light exiting the light-emitting element 501 is illuminated to the solder material 300c through the mirror 502a, 502b. Due to this, there is light reflection from the solder material 300c, the reflection light is guided to the diffraction grating 503a through the mirror 502c, 502d.

Furthermore, the diffraction grating 503a diffracts the particular wave-number band of infrared light from the mirror 502d to the mirror 503b. The mirror 503b guides the infrared radiation to the light-receiving part of the light-receiving element 505. Due to this, of the light reflected by the solder material 300c in the printer 300, an infrared radiation can be guided to the light-receiving part of the light-receiving element 505, thus enabling in-line analysis.

The invention is not limited to the embodiments described above but can be modified in various ways within the scope of the invention. The embodiments, obtained by properly combining the technical means disclosed in the embodiments, are included in the technical scope of the invention.

Incidentally, the control section 15 in the embodiment can be realized by executing the program stored in the storage means such as ROM (read only memory) and RAM due to the operation means such as the CPU and controlling the input means such as a keyboard, output means such as a display or the communicating means such as an interface circuit. Accordingly, by merely reading a recording medium storing the program and executing the program due to a computer having those means, the various functions of and processing in the control section 15 can be realized. Meanwhile, by recording the program on a removable recording medium, the various functions and processes can be realized on a desired computer.

The recording medium may be a program media such as a memory not-shown, e.g. ROM, because to be processed by the microcomputer, or a program media that, although not shown, a program reader is provided as an external storage device so that reading is possible by inserting the recording medium therein.

In both cases, the program stored is preferably structured executable by accessing from a microprocessor. Furthermore, even if the program can be downloaded from the network, it is desirable that the download program is assumed previously stored in the apparatus beforehand or the download program is installed by another recording medium.

Meanwhile, as the program media, there is a recording medium structured separable from the main body which recording medium, etc. fixedly carries a program including those based on a tape, e.g. a magnetic tape or a cassette tape, a disk, e.g. a magnetic disk including a flexible disk, a hard disk or a CD/MO/MD/DVD disk, a card, e.g. an IC card (including a memory card), or a semiconductor memory, e.g. a mask ROM, an EPROM (erasable programmable read only memory), an EEPROM (electrically erasable programmable read only memory) or a flash ROM.

Meanwhile, provided that in a system structure connectable with a communication network including the Internet, preferred is a recording medium fluidly carrying a program in a manner downloading a program from a communication network.

Furthermore, where downloading a program from a communication network in this manner, the downloading program preferably is stored in the present apparatus in advance or installed from a separate recording medium.

The solder material test method and apparatus of the invention is suited as a method and apparatus that conducts a test of a pasty solder material for use in a printing process on a print board production line, but can be broadly applied generally to the well known solder materials without limited to such a pasty solder material.

The invention claimed is:

1. A solder material test method including:
    a first detecting step of detecting a first intensity at a particular wave number of infrared ray reflected from a test-sample solder material by illuminating light to the test-sample solder material; and
    a test step of testing a deterioration degree of the test-sample solder material relatively to a comparative-sample solder material, depending upon the first intensity detected.

2. A solder material test method according to claim 1, wherein the particular wave number is included in a range of 520 cm-1 to 700 cm-1.

3. A solder material test method according to claim 1, wherein the particular wave number is included in a range of 1270 cm-1 to 1430 cm-1.

4. A solder material test method according to claim 1, wherein the particular wave number is included in a range of 1500 cm-1 to 1650 cm-1.

5. A solder material test method according to claim 1, wherein the particular wave number is included in a range of 1665 cm-1 to 1730 cm-1.

6. A solder material test method according to claim 1, wherein the particular wave number is included in a wave number band that an infrared ray is to be absorbed by a metal oxide contained in the solder material.

7. A solder material test method according to claim 6, wherein the metal oxide is tin oxide.

8. A solder material test method according to claim 1, wherein the particular wave number is included in a wave number band that an infrared ray is to be absorbed by a salt contained in the solder material.

9. A solder material test method according to claim 8, wherein the salt is carboxylate.

10. A solder material test method according to claim 1, wherein the particular wave number is included in a wave number band that an infrared ray is to be absorbed by an acid contained in the solder material.

11. A solder material test method according to claim 10, wherein the acid is carboxylic acid.

12. A solder material test method according to claim 1, further comprising a second detecting step of detecting a second intensity at the particular wave number of infrared ray reflected from the comparative-sample solder material by illuminating light to the comparative-sample solder material, and
wherein the test step of testing a deterioration degree of the test-sample solder material relatively to the comparative-sample solder material, depends upon both the first and second intensities detected.

13. A solder material test method according to claim 12, wherein the test step is to determine a difference between the first intensity and the second intensity.

14. A solder material test method according to claim 13, wherein a reference wave number is different in wave number from the particular wave number, the first detecting step being to detect further a third intensity at the reference wave number of infrared ray reflected from the test-sample solder material, the second detecting step being to detect further a fourth intensity at the reference wave number of infrared ray reflected from the comparative-sample solder material, the test step correcting at least any of the first and second intensities depending upon a difference between the third and fourth intensities.

15. A solder material test method according to claim 12, wherein the test step is to determine a ratio of the first intensity and the second intensity.

16. A solder material test method according to claim 12, wherein the test step is to determine a first infrared ray absorbance at the particular wave number to the test-sample solder material depending upon the first intensity, and a second infrared ray absorbance at the particular wave number to the comparative-sample solder material depending upon the second intensity, thereby determining a difference between the first infrared ray absorbance and the second infrared ray absorbance.

17. A solder material test method according to claim 16, wherein a reference wave number is different in wave number from the particular wave number, the first detecting step being to detect further a third intensity at the reference wave number of infrared ray reflected from the test-sample solder material, the second detecting step being to detect further a fourth intensity at the reference wave number of infrared ray reflected from the comparative-sample solder material, the test step being to determine a third infrared ray absorbance at the reference wave number to the test-sample solder material depending upon the third intensity, and a fourth infrared ray absorbance at the reference wave number to the test-sample solder material depending upon the fourth intensity, thereby correcting at least any of the first and second infrared ray absorbances depending upon a difference between the third infrared ray absorbance and the fourth infrared ray absorbance.

18. A solder material test method according to claim 12, wherein the test step is to determine a first infrared ray absorbance at the particular wave number to the test-sample solder material depending upon the first intensity, and a second infrared ray absorbance at the particular wave number to the comparative-sample solder material depending upon the second intensity, thereby determining a ratio of the first infrared ray absorbance and the second infrared ray absorbance.

19. A solder material test apparatus comprising:
a light source that illuminates light to a test-sample solder material and a comparative-sample solder material;
intensity detecting means that detects a first intensity at a particular wave number of infrared ray reflected from the test-sample solder material due to illumination of the light; and
control means that outputs a deterioration parameter indicative of a comparative deterioration degree of the test-sample solder material relatively to the comparative-sample solder material.

20. A computer-readable recording medium storing a program for use with the solder material test apparatus of claim 19, the program when executed by a computer of the test apparatus causing the control means to perform the process of outputting the deterioration parameter indicative of the comparative deterioration degree of the test-sample solder material relatively to the comparative-sample solder material.

21. A solder material test apparatus according to claim 19, wherein the intensity detecting means further detects a second intensity at the particular wave number of infrared ray reflected from the comparative-sample solder material due to illumination of the light.

22. A solder material test method comprising:
detecting a first intensity at a particular wave number of infrared ray reflected from a test-sample solder material; and
testing a deterioration degree of the test-sample solder material depending upon the first intensity detected.

23. A solder material test apparatus comprising:
an intensity detector that detects a first intensity at a particular wave number of infrared ray reflected from a test-sample solder material; and
a controller that outputs a deterioration parameter indicative of a deterioration degree of the test-sample solder material based on the first intensity detected.

* * * * *